United States Patent
Walter

(10) Patent No.: US 10,213,533 B2
(45) Date of Patent: Feb. 26, 2019

(54) MEDICAL TOOLS WITH ASPIRATION TIPS SUITABLE FOR CATARACT SURGERIES AND RELATED METHODS

(71) Applicant: Wake Forest University Health Sciences, Winston-Salem, NC (US)

(72) Inventor: Keith Andrew Walter, Lewisville, NC (US)

(73) Assignee: Keith A. Walter, Lewisville, NC (US)

( * ) Notice: Subject to any disclaimer, the term of this patent is extended or adjusted under 35 U.S.C. 154(b) by 743 days.

(21) Appl. No.: 14/483,626

(22) Filed: Sep. 11, 2014

(65) Prior Publication Data

US 2015/0005753 A1     Jan. 1, 2015

Related U.S. Application Data

(63) Continuation-in-part of application No. 13/783,775, filed on Mar. 4, 2013.

(60) Provisional application No. 61/606,648, filed on Mar. 5, 2012, provisional application No. 61/877,447, filed on Sep. 13, 2013.

(51) Int. Cl.
| | |
|---|---|
| *A61M 1/00* | (2006.01) |
| *A61F 9/008* | (2006.01) |
| *A61F 9/007* | (2006.01) |
| *A61M 3/02* | (2006.01) |

(52) U.S. Cl.
CPC ......... *A61M 1/008* (2013.01); *A61F 9/00745* (2013.01); *A61F 9/00834* (2013.01); *A61M 3/0283* (2013.01); *A61F 9/008* (2013.01); *A61F 9/00825* (2013.01); *A61F 2009/0087* (2013.01); *A61F 2009/00887* (2013.01)

(58) Field of Classification Search
CPC ............. A61F 9/00745; A61F 9/00834; A61B 10/0275
See application file for complete search history.

(56) References Cited

U.S. PATENT DOCUMENTS

| | | | | |
|---|---|---|---|---|
| 693,358 | A * | 2/1902 | Westlake | A61M 3/0283 604/39 |
| 3,809,093 | A * | 5/1974 | Abraham | A61F 9/00763 606/169 |
| 3,937,222 | A * | 2/1976 | Banko | A61F 9/00763 606/107 |
| 3,958,573 | A * | 5/1976 | Wiley | A61C 17/04 604/267 |
| 3,996,935 | A * | 12/1976 | Banko | A61B 17/32002 604/22 |
| 4,011,869 | A * | 3/1977 | Seiler, Jr. | A61F 9/00763 604/22 |

(Continued)

OTHER PUBLICATIONS

MicroSurgical Technology "Duet® BiManual I/A" *Product Webpage* http://www.microsurgical.com/products/duet-bemanual-i-a (5 pages) (date unknown; printed from the internet Jan. 8, 2015).

(Continued)

*Primary Examiner* — Bhisma Mehta
*Assistant Examiner* — Matthew A Engel
(74) *Attorney, Agent, or Firm* — Myers Bigel, P.A.

(57) ABSTRACT

Devices and methods for cataract surgery include a tip with reciprocating door to chop, fragment or reduce size of large nuclear lens fragments and/or cortex fragments in a capsule bag to facilitate aspiration.

15 Claims, 18 Drawing Sheets

(56) References Cited

U.S. PATENT DOCUMENTS

| | | | | |
|---|---|---|---|---|
| 4,044,119 A * | 8/1977 | Carlson, Jr. | A61K 9/0068 | 424/438 |
| 4,240,434 A * | 12/1980 | Newkirk | A61F 2/2412 | 137/242 |
| 4,331,130 A * | 5/1982 | Lewicky | A61F 9/00736 | 604/23 |
| 4,340,037 A * | 7/1982 | Lewicky | A61F 9/00736 | 600/20 |
| 4,368,734 A * | 1/1983 | Banko | A61F 9/00763 | 606/107 |
| 4,515,583 A * | 5/1985 | Sorich | A61F 9/00745 | 604/22 |
| 4,548,205 A * | 10/1985 | Armeniades | A61B 3/16 | 600/488 |
| 4,578,059 A * | 3/1986 | Fabricant | A61F 9/00736 | 604/289 |
| 4,634,420 A * | 1/1987 | Spinosa | A61F 9/00745 | 433/119 |
| 4,678,459 A * | 7/1987 | Onik | A61B 17/32002 | 604/22 |
| 4,681,561 A * | 7/1987 | Hood | A61B 17/22012 | 433/119 |
| 4,694,828 A * | 9/1987 | Eichenbaum | A61F 9/008 | 606/6 |
| 4,808,154 A * | 2/1989 | Freeman | A61M 1/0084 | 604/22 |
| 4,825,865 A * | 5/1989 | Zelman | A61F 9/00736 | 604/266 |
| 4,842,589 A * | 6/1989 | Fecht | A61M 27/00 | 604/523 |
| 4,883,699 A * | 11/1989 | Aniuk | A61L 29/049 | 428/36.9 |
| 4,921,477 A | 5/1990 | Davis | | |
| 5,057,098 A * | 10/1991 | Zelman | A61F 9/00736 | 604/22 |
| 5,087,265 A * | 2/1992 | Summers | A61B 17/320758 | 604/22 |
| 5,112,301 A * | 5/1992 | Fenton, Jr. | A61M 1/008 | 604/247 |
| 5,112,339 A * | 5/1992 | Zelman | A61F 9/00745 | 606/107 |
| 5,139,504 A * | 8/1992 | Zelman | A61F 9/00736 | 606/107 |
| 5,188,589 A * | 2/1993 | Wypych | A61F 9/00745 | 604/22 |
| 5,199,943 A * | 4/1993 | Wypych | A61F 9/00745 | 604/22 |
| 5,209,719 A * | 5/1993 | Baruch | A61B 17/22012 | 604/22 |
| 5,360,397 A * | 11/1994 | Pinchuk | A61M 5/1582 | 604/266 |
| 5,487,725 A * | 1/1996 | Peyman | A61F 9/00727 | 604/22 |
| 5,505,693 A * | 4/1996 | Mackool | A61F 9/00745 | 604/22 |
| 5,527,332 A * | 6/1996 | Clement | A61B 17/320016 | 604/35 |
| 5,599,306 A * | 2/1997 | Klein | A61M 25/104 | 604/103.01 |
| 5,718,677 A * | 2/1998 | Capetan | A61M 1/008 | 604/239 |
| 5,741,275 A * | 4/1998 | Wyssmann | A61M 5/14526 | 604/143 |
| 5,772,629 A * | 6/1998 | Kaplan | A61K 38/57 | 514/14.5 |
| 5,782,849 A * | 7/1998 | Miller | A61B 17/32002 | 604/22 |
| 5,792,167 A * | 8/1998 | Kablik | A61B 17/32002 | 604/22 |
| 5,810,869 A * | 9/1998 | Kaplan | A61M 25/0014 | 604/96.01 |
| 5,814,010 A * | 9/1998 | Ziegler | A61F 9/00745 | 604/22 |
| 5,814,020 A * | 9/1998 | Gross | A61M 5/14248 | 604/141 |
| 5,817,099 A * | 10/1998 | Skolik | A61B 17/3462 | 604/22 |
| 5,824,002 A * | 10/1998 | Gentelia | A61B 17/3417 | 604/164.11 |
| 5,873,851 A | 2/1999 | Nilsson | | |
| 5,906,599 A * | 5/1999 | Kaldany | A61D 7/00 | 604/264 |
| 5,911,701 A * | 6/1999 | Miller | A61B 17/32002 | 604/22 |
| 5,941,887 A * | 8/1999 | Steen | A61F 9/00745 | 604/22 |
| 5,971,959 A * | 10/1999 | Liu | A61M 25/0631 | 604/164.01 |
| 5,984,904 A * | 11/1999 | Steen | A61F 9/00745 | 604/22 |
| 6,033,379 A * | 3/2000 | Barra | A61M 25/10 | 604/103.11 |
| 6,159,175 A * | 12/2000 | Strukel | A61M 1/0035 | 604/118 |
| 6,454,763 B1 * | 9/2002 | Motter | A61F 9/00802 | 606/15 |
| 6,589,200 B1 * | 7/2003 | Schwemberger | A61B 17/320068 | 600/459 |
| 6,659,996 B1 * | 12/2003 | Kaldany | A61B 17/3468 | 604/103.06 |
| 6,695,821 B1 * | 2/2004 | Sjaarda | A61M 3/0279 | 604/264 |
| 6,852,093 B1 | 2/2005 | Boukhny | | |
| 6,958,056 B2 * | 10/2005 | Kadziauskas | A61F 9/00745 | 604/272 |
| 7,074,213 B2 * | 7/2006 | McGuckin, Jr. | A61M 1/285 | 604/264 |
| 7,135,009 B2 * | 11/2006 | Tu | | 604/27 |
| 7,402,156 B2 * | 7/2008 | Kiehlbauch | A61F 9/0026 | 600/236 |
| 7,806,865 B1 * | 10/2010 | Wilson | A61F 9/00745 | 604/131 |
| 7,967,775 B2 | 6/2011 | Hong | | |
| 8,070,711 B2 * | 12/2011 | Bassinger | A61M 1/0062 | 604/22 |
| 8,262,585 B2 * | 9/2012 | Thompson | A61B 10/0275 | 600/564 |
| 8,282,594 B2 * | 10/2012 | Perkins | A61M 3/0279 | 604/22 |
| 8,303,549 B2 * | 11/2012 | Mejlhede | A61M 5/142 | 604/180 |
| 8,414,605 B2 * | 4/2013 | Gordon | A61F 9/00745 | 606/169 |
| 9,308,358 B2 * | 4/2016 | Oliver | A61F 9/00772 | |
| 9,693,898 B2 * | 7/2017 | Farley | A61F 9/00763 | |
| 9,707,012 B2 * | 7/2017 | Adams | A61B 17/42 | |
| 2002/0111586 A1 * | 8/2002 | Mosel | A61B 5/202 | 604/174 |
| 2002/0121281 A1 * | 9/2002 | Humayun | A61M 1/008 | 128/898 |
| 2002/0151917 A1 * | 10/2002 | Barry | A61B 17/320758 | 606/159 |
| 2002/0183722 A1 * | 12/2002 | Harper | A61M 5/14276 | 604/892.1 |
| 2004/0193121 A1 * | 9/2004 | Kadziauskas | A61M 1/008 | 604/272 |
| 2005/0226814 A1 * | 10/2005 | Levy | A61K 49/0004 | 424/9.1 |
| 2005/0277898 A1 * | 12/2005 | Dimalanta | A61F 9/00736 | 604/275 |
| 2006/0100653 A1 * | 5/2006 | Akahoshi | A61F 9/00745 | 606/169 |
| 2006/0200042 A1 * | 9/2006 | Weikel, Jr. | A61B 10/0275 | 600/566 |
| 2006/0253056 A1 * | 11/2006 | Kadziauskas | A61F 9/00745 | 602/22 |

(56) References Cited

U.S. PATENT DOCUMENTS

| | | | | |
|---|---|---|---|---|
| 2007/0185454 A1* | 8/2007 | Fangrow, Jr. | A61M 5/158 | 604/164.01 |
| 2008/0039792 A1* | 2/2008 | Meng | A61K 9/0024 | 604/114 |
| 2008/0167604 A1* | 7/2008 | Hong | A61F 9/00745 | 604/27 |
| 2009/0054904 A1 | 2/2009 | Holmen | | |
| 2009/0093789 A1* | 4/2009 | Dacquay | A61F 9/0017 | 604/506 |
| 2010/0121260 A1 | 5/2010 | Ghannoum et al. | | |
| 2011/0137231 A1* | 6/2011 | Sorensen | A61F 9/00745 | 604/22 |
| 2012/0065578 A1* | 3/2012 | Zhou | A61M 1/0064 | 604/22 |
| 2012/0157934 A1* | 6/2012 | Liao | A61F 9/00745 | 604/264 |
| 2012/0172786 A1* | 7/2012 | Mackool | A61M 1/0084 | 604/22 |
| 2012/0203198 A1* | 8/2012 | Searle | A61M 5/14248 | 604/506 |
| 2013/0231605 A1* | 9/2013 | Walter | A61M 3/0283 | 604/22 |
| 2013/0317476 A1* | 11/2013 | Searle | A61M 25/0045 | 604/506 |
| 2014/0074013 A1* | 3/2014 | McCary | A61F 9/00745 | 604/22 |
| 2015/0005753 A1* | 1/2015 | Walter | A61F 9/00834 | 606/6 |
| 2015/0025564 A1* | 1/2015 | Tsutsui | A61M 25/1002 | 606/194 |
| 2015/0297407 A1* | 10/2015 | Saimovici | A61F 9/00745 | 606/107 |

OTHER PUBLICATIONS

International Search Report and Written Opinion for related PCT application No. PCT/US2014/055115, dated Dec. 19, 2014, 14 pages.

BD Visitec™ Capsule Polisher [Kratz] from Beaver-Visitec International, Product Example, http://www.ophthalmologyweb.com/5466-Capsule-Scraper-and-Poli . . . , date unknown, printed from the internet Mar. 2, 2012.

Cataract Product Catalog, Alcon®, 2008/2009, 65 pages.

Nagy, et al., Initial Clinical Evaluation of an Intraocular Femtosecond Laser in Cataract Surgery, Journal of Refractive Surgery, Dec. 2009, vol. 25, pp. 1053-1060.

International Search Report and Written Opinion for corresponding PCT Application No. PCT/US2013/028927, dated Jul. 18, 2013.

* cited by examiner

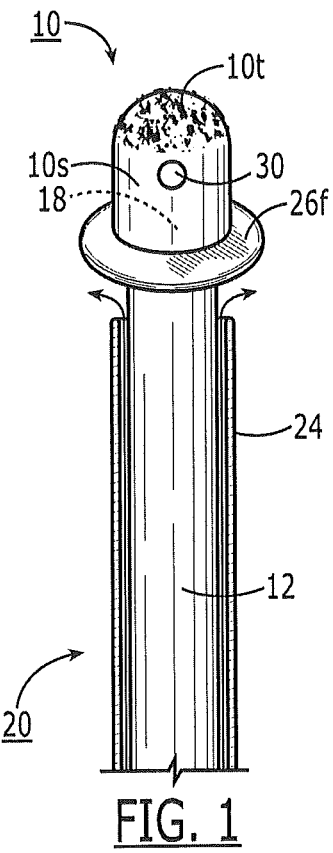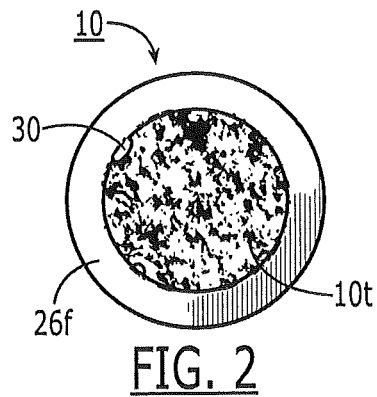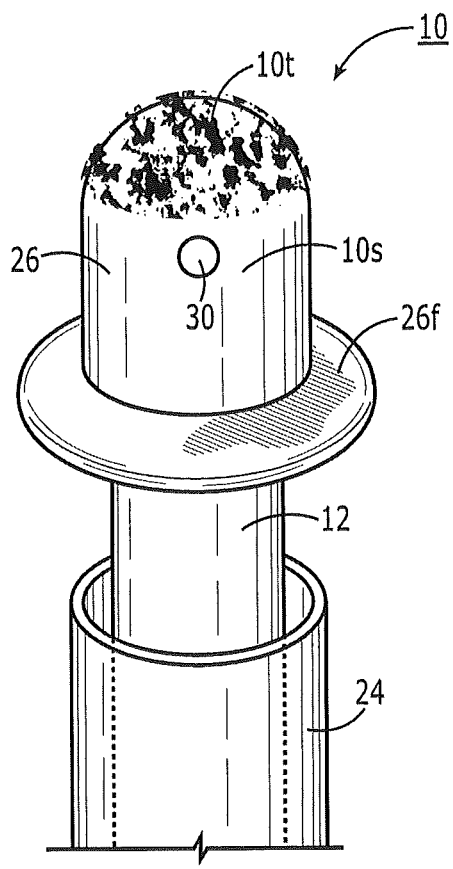
FIG. 1
FIG. 2
FIG. 3

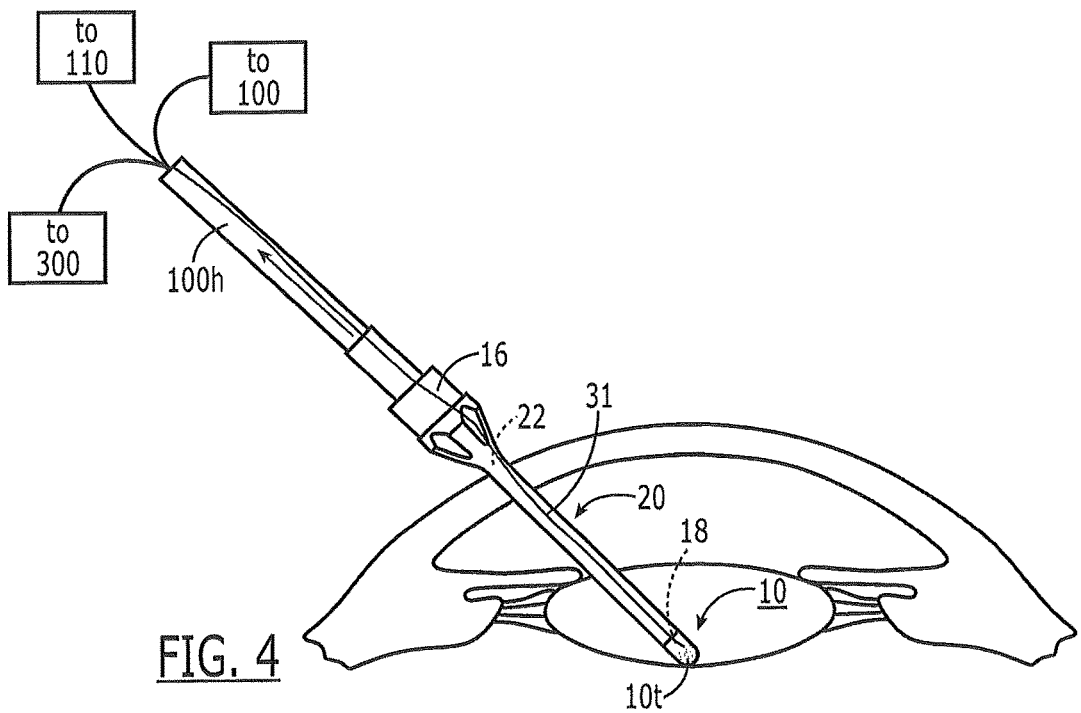
FIG. 4
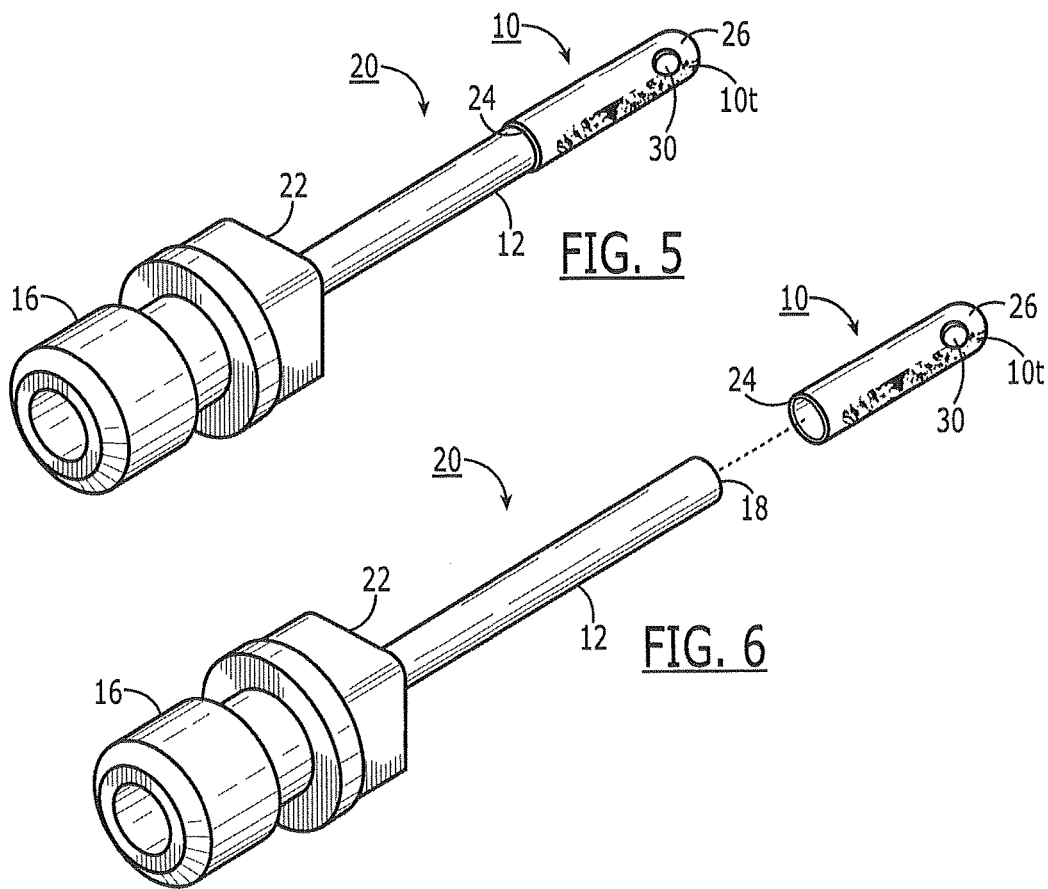
FIG. 5
FIG. 6

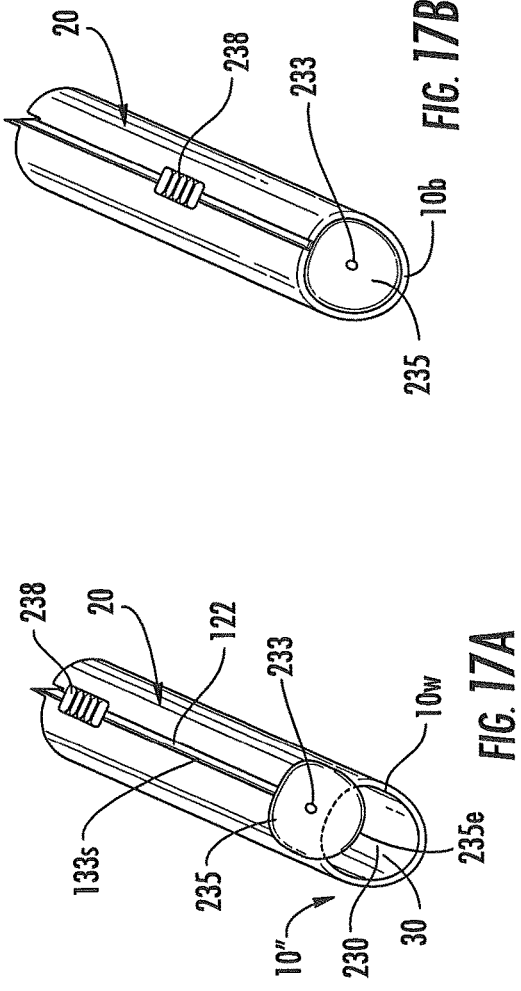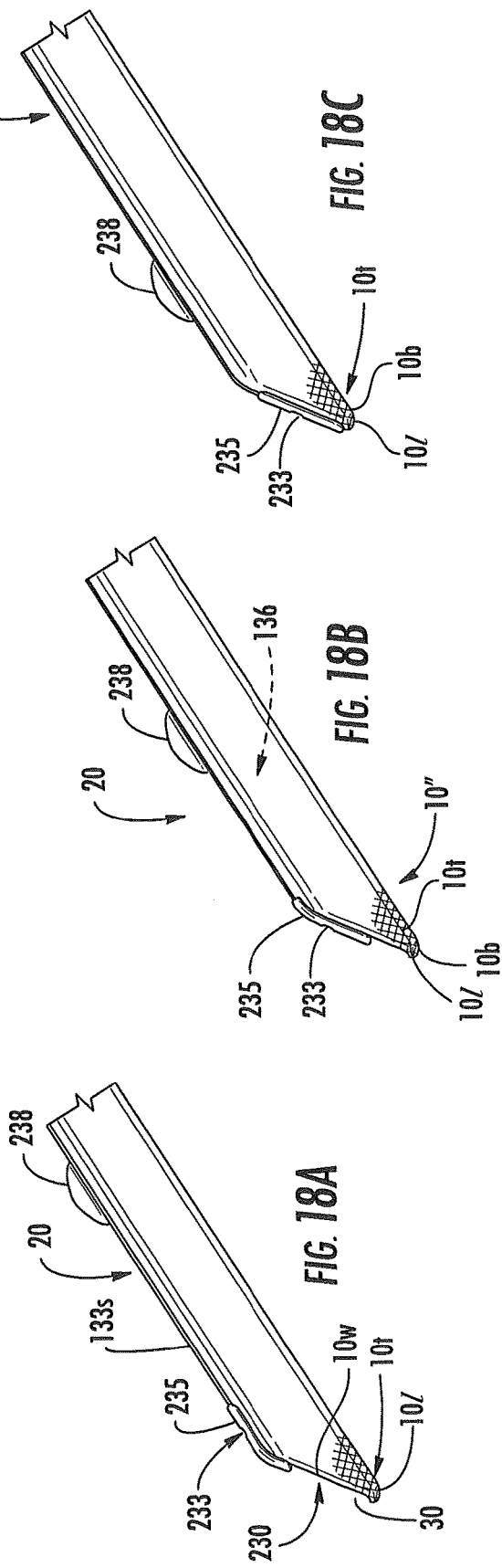

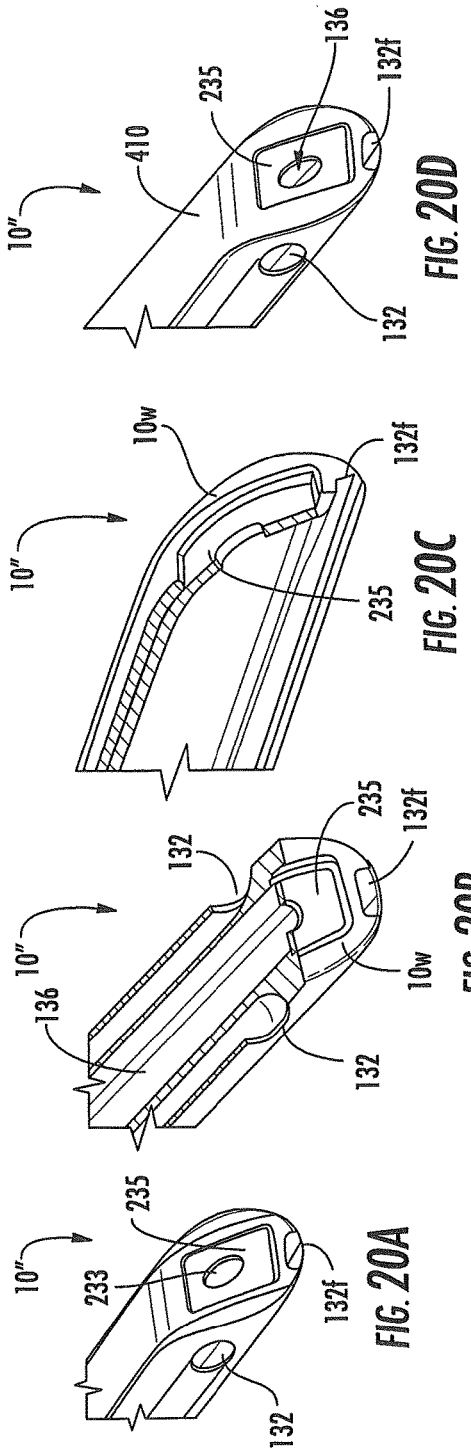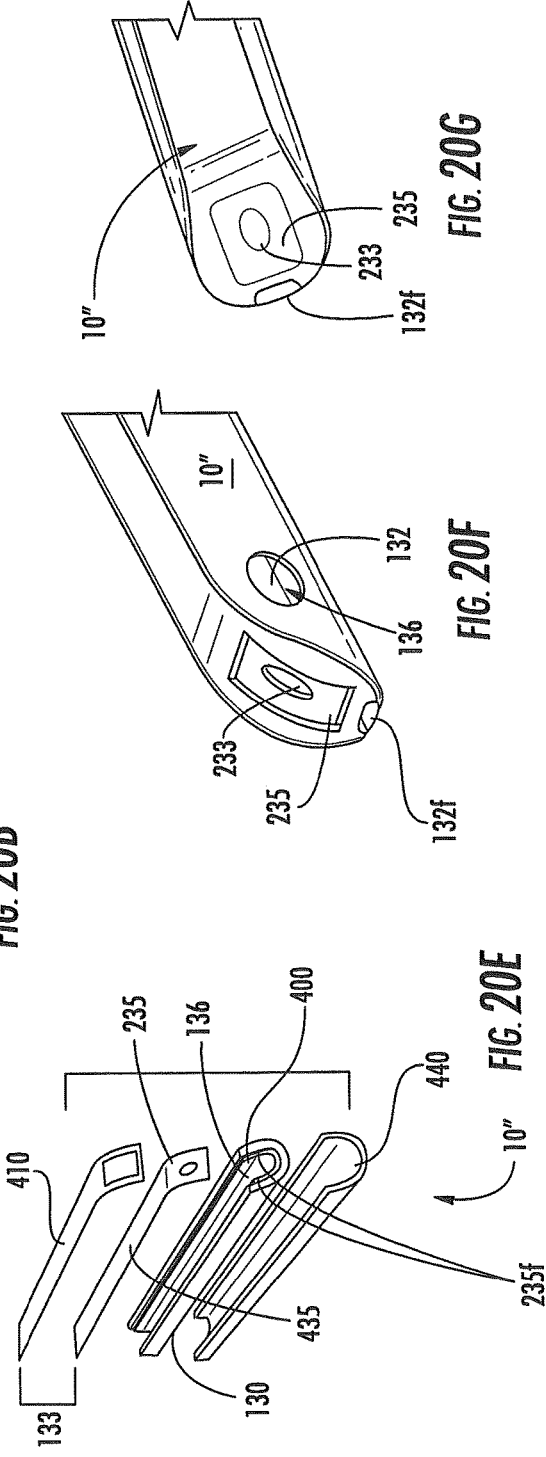

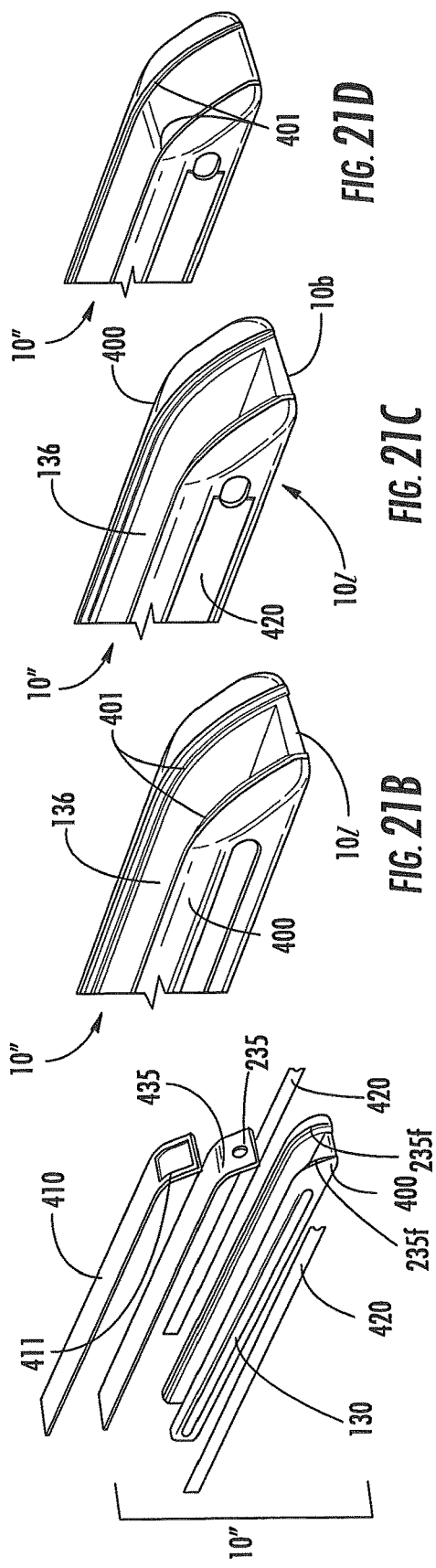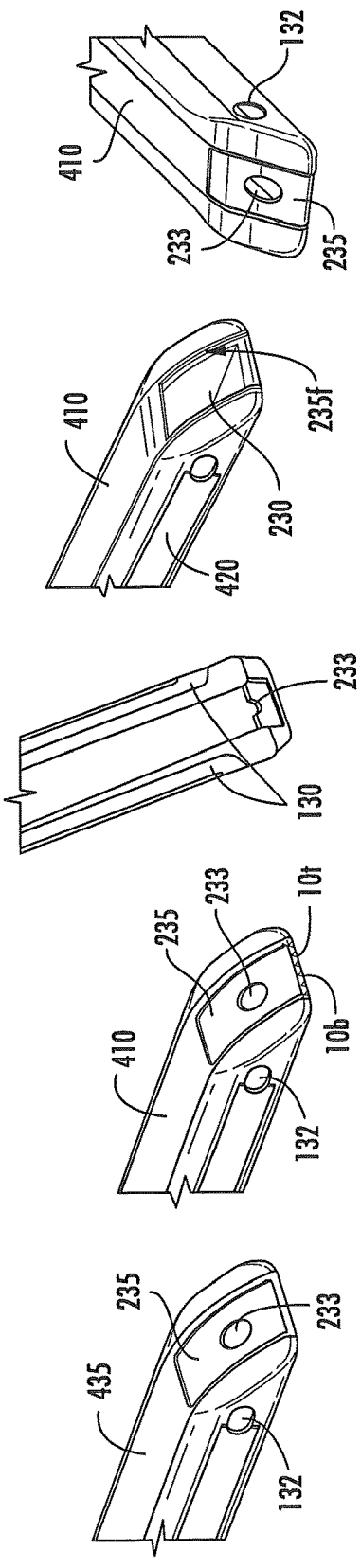

MEDICAL TOOLS WITH ASPIRATION TIPS SUITABLE FOR CATARACT SURGERIES AND RELATED METHODS

RELATED APPLICATIONS

This application is a continuation-in-part of U.S. patent application Ser. No. 13/783,775, filed Mar. 4, 2013, which claims the benefit of and priority to U.S. Provisional Application Ser. No. 61/606,648, filed Mar. 5, 2012, the contents of which are hereby incorporated by reference as if recited in full herein. This application also claims the benefit of and priority to U.S. Provisional Application Ser. No. 61/877,447, filed Sep. 13, 2013, the contents of which are also hereby incorporated by reference as if recited in full herein.

FIELD OF THE INVENTION

This invention relates to aspiration tips that are particularly suitable for use in ophthalmic surgery such as, for example, phacoemulsification including ultrasonic and femtosecond laser cataract surgery.

BACKGROUND OF THE INVENTION

In the United States, the majority of cataract lenses are removed by a surgical procedure known as phacoemulsification. During this procedure, a cutting tip is inserted into the diseased lens and vibrated ultrasonically. The vibrating cutting tip liquefies or emulsifies the lens so that the lens can be aspirated out of the eye. The diseased lens, once removed, is then typically replaced by an artificial lens.

More recently, femtosecond lasers have been proposed for use in cataract surgeries. The femtosecond laser has the capability to assist the fragmentation (laser phacoemulsification or breaking up) of the cataract. Generally stated, the laser applies a number of pulses to the lens in a pre-designed pattern which then allows the surgeon to remove the lens matter. See, e.g., Nagy et al, Initial clinical evaluation of an intraocular femtosecond laser in cataract surgery. J Refract Surg 2009; 25:1053-60.

Prior to inserting the artificial lens, softer or attached cortical material that was not removed during the initial step is aspirated from the eye. Typically, this is done using a tip that is similar to the ultrasound phacoemulsification tip, but with a smaller opening at the distal end and without the ultrasonic vibration. The aspiration tip can also be used to polish the posterior capsule to remove residual cortical fibers or epithelium cells to reduce the risk of posterior capsule opacification or other undesired events. Conventional aspiration tips have been made from titanium or stainless steel with highly polished surfaces to reduce burrs or sharp edges. Other aspiration tips use silicone rubber tip caps that reside over the metal tips. See, U.S. Pat. No. 5,718,677. More recently, dual function aspiration tips such as the MicroSmooth® sleeve from Alcon, Inc., that can both irrigate and aspirate have been used. See also, U.S. Pat. No. 7,967,775. The contents of these patent documents are hereby incorporated by reference as if recited in full herein.

Despite the above tips, often a J-shaped cannula or other tool must be inserted into the capsule bag during capsule polishing to help detach cortical material that is resistant to aspiration using just the aspiration and irrigation tip. Thus, there remains a need for tips that can facilitate cortical clean-up and/or polishing of the capsule bag to prevent posterior capsular opacification.

SUMMARY OF EMBODIMENTS OF THE INVENTION

Embodiments of the invention are directed to providing an aspiration tip that can be used during cataract surgeries.

Embodiments of the invention provide surgical tools suitable for aspirating and/or polishing of a capsule bag during ophthalmic cataract surgery.

Embodiments of the invention are directed to methods of performing cataract surgery. The methods include: (a) performing a phacoemulsification or laser disintegration procedure on an eye of a patient; (b) inserting, in vivo, a tip of an aspiration tool into a posterior capsule bag of a patient. The tool tip has an open leading end that defines an aspiration port and the tip includes a longitudinally translatable door. The method also includes (c) aspirating nuclear lens fragments using the aspiration port; and (d) manually or automatically directing the door to reciprocate in a longitudinal direction to at least partially close, then open, the aspiration port to thereby reduce size of at least some nuclear lens fragments.

The door can include at least one aspiration port that is smaller than the leading end aspiration port. The method can include, after the automatically or manually directing step, manually or automatically closing the door over the large aspiration port, then aspirating cortical material with the door closed through the aspiration port in the door.

The tip can include external surface texture. The method can include polishing the posterior capsule using the textured external surface.

The door can be flexible and can reciprocate manually and/or automatically before, during or after the aspirating.

The tip can have a textured external portion and a smooth surface portion. The method can include rotating the tip so that the textured surface faces cortical tissue after the inserting step for capsular polishing.

The manually or automatically directing the door to reciprocate can be carried out to move a leading end of the door aft and forward a distance between about 0.5 mm and about 2 mm to chop nuclear lens fragments to reduce the size of the nuclear lens fragments proximate the aspiration port.

The door can include at least one aspiration port that is smaller than the leading end aspiration port, the method further comprising aspirating cortex material through the smaller aspiration port when the door resides over the leading end aspiration port.

The door can have a pair of opposing outer side edges that slidably engage a respective side door frame in the tool tip during the reciprocal movement.

The tip can include at least one irrigation port. The method can include flowing irrigation fluid out of the at least one irrigation port during the aspirating.

The tip can include a front irrigation port. The method can include flowing irrigation fluid out of the front irrigation port during the aspirating.

Other embodiments are directed to an aspiration tool for use in combination with a surgical system for cataracts after a phacoemulsification or laser disintegration procedure. The aspiration tool includes a tip having an open leading end defining a first aspiration port, the tip sized and configured for removing cortical (e.g., nuclear lens) fragments, tissue and/or fibers. The tool also includes a translatable door in communication with the first aspiration port configured to extend and retract about the first aspiration port. In the extended position, the door travels forward to at least partially occlude the first aspiration port.

The open leading end, when viewed from the side, can have a tapered or angled profile that travels from an upper surface to a lower leading edge.

The open leading end of the tip can have an external planar bottom surface.

The first aspiration port can have a perimeter that has spaced apart sides with guides, channels or rails that engage outer side edges of the door to allow the door to slidably translate up and down.

The door can have a planar bottom end that is sized and configured to close against a bottom surface of the leading end of the tip.

The door can have at least one aspiration port extending therethrough. The door aspiration port can have a size that is smaller than the first aspiration port. The first aspiration port has a width that is between about 1 mm to about 1.5 mm across and a height that is between about 0.7 to about 1 mm.

At least a portion of the leading end of the tip can have a textured exterior surface.

The textured surface can extend about at least a portion of a perimeter of the door and/or an external wall of the leading end of the tip adjacent the perimeter of the door.

The tool can have a user control in communication with the door. The translatable door can be configured to oscillate or reciprocate over the first aspiration port responsive to input with the user control. The user control can include at least one of an electronic or manual control.

The door can be flexible and can extend to be flat across the aspiration port when closed.

The door can have a pair of opposing outer side edges that each slidably engage a respective side door frame in the tool tip during the reciprocal movement.

The tip can include at least one irrigation port in fluid communication with a fluid irrigation channel.

The leading end of the tip can include a front irrigation port.

The tip can include an elongate primary body defining an interior aspiration channel with a pair of spaced apart longitudinally extending guides, channels or rails that extend downward in a distal end thereof to define first and second sides of a door frame for slidably engaging respective outer spaced apart sides of the door.

The door can have a longitudinally extending shaft or extension that cooperates with the longitudinally extending guides, channels or rails and a user control to translate the door between extended and retracted positions.

The door can be configured to be flat across the aspiration port to close the aspiration port. The door can includes an aspiration port that is smaller than the first aspiration port and resides over the first aspiration port when the door is in an extended configuration.

Other embodiments are directed to an ophthalmic irrigation/aspiration device. The device includes an aspiration cannula, the cannula having a hub configured to attach to a hand piece and an open end opposite the hub; and a tip adapted to enter a capsular bag of an eye of a patient, the tip residing over the open end of the aspiration cannula. The tip has a leading open end that forms an aspiration port.

When viewed from a side, the forward leading end can taper or angle down to a forwardmost segment that is typically a bottom end segment. The tip includes a longitudinally translating door that is sized and configured to oscillate and/or reciprocate over the aspiration port to thereby chop and/or crush nuclear lens fragments in an eye of a patient.

Embodiments of the invention provide surgical tools suitable for facilitating the dismantling or aspiration of a lens during laser-phaco surgery, such as during or after femtosecond laser treatment for cataract surgery to remove nuclear fragments and/or epinucleus.

Some aspects are directed to methods of performing cataract surgery. The methods include: (a) performing a phacoemulsification procedure on an eye of a patient; then (b) inserting, in vivo, an elastomeric tip of an aspiration/irrigation tool having a textured patch on an outer surface thereof into a capsule bag of a patient; then (c) manually moving the tip to cause the textured surface to contact cortical tissue; and then (d) aspirating cortical tissue using the tip.

The tip can have a non-textured smooth outer surface proximate the irrigation/aspiration port and the smooth outer surface can cover a greater surface area than a surface area of the textured patch.

The textured patch can reside only on a distalmost end of the tip.

The textured patch can cover only a rounded distal end of the tip a distance forward of the aspiration portion.

The tip can have a smooth surface opposite the textured patch, the method comprising rotating the tip so that the textured surface faces the cortical tissue after the inserting step.

Other embodiments are directed to multi-purpose irrigation/aspiration tips for use in combination with a surgical system for cataracts. The tips include an external elastomeric end cap having opposing proximal and distal end portions, the distal end portion having an aspiration port and a textured patch on an outer surface, the end cap sized and configured for polishing a capsular bag and/or contacting cortical fibers using the textured surface.

The textured patch can reside only on a distalmost end of the end cap.

The textured patch can cover only a rounded distal end of the end cap a distance forward of the aspiration portion.

The textured surface can be spaced apart between about 0.1 mm to about 5 mm from the aspiration port and other than the textured patch, the end cap has a smooth outer surface.

The distal end portion of the end cap can have a surface area and the textured patch surface occupies less than half the surface area.

The textured patch can occupy an elongate area of a sub-portion of the distal end portion of the end cap with the end cap having a non-textured smooth surface for at least a major portion of a surface area of the end cap.

Still other embodiments are directed to ophthalmic irrigation/aspiration devices. The devices include: an aspiration cannula, the cannula having a hub configured to attach to a handpiece and an open end opposite the hub; and a removable, external elastomeric tip adapted to enter a capsular bag of an eye of a patient, the tip sealing the open end of the cannula and characterized in that the tip comprises a distal end portion with an outer surface having a textured patch.

The textured patch can reside only on a distalmost end of the tip.

The textured patch can cover only a rounded distal end of the tip a distance forward of the aspiration portion.

The textured surface can be spaced apart between about 0.1 mm to about 5 mm from the aspiration port and other than the textured patch, the tip has a smooth outer surface.

The distal end portion of the tip can have a surface area, and wherein the textured patch surface occupies less than half the surface area.

The textured patch can occupy an area of a sub-portion of the distal end portion of the tip with the tip having a non-textured smooth surface for at least a major portion of a surface area of the tip.

The tip can include an end cap with a flange that is coupled to the cannula through a friction-fit between a portion of the end cap and the cannula, wherein, wherein the aspiration port is located at a distal tip of the end cap and the textured patch resides forward of the aspiration port on the tip.

The tip can include a sleeve that is external to the hub and hand piece, the sleeve further comprising a fluid irrigation channel and at least one associated port.

The textured surface can be spaced apart between about 0.1 mm to about 1 mm from a distal end of the tip.

The textured patch can occupy less than half a surface area of the distal end of the tip.

The textured patch can occupy an elongate narrow strip area of a sub portion of the distal end portion of the tip.

The end cap can be rubber.

The foregoing and other objects and aspects of the present invention are explained in detail in the specification set forth below.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

FIG. 1 is a side schematic partial cutaway view of a device with an aspiration/irrigation tip according to embodiments of the present invention.

FIG. 2 is an end view of the device shown in FIG. 1.

FIG. 3 is a greatly enlarged view of the device shown in FIGS. 1 and 2.

FIG. 4 is a schematic illustration of a surgical aspiration tip suitable for cataract surgery according to embodiments of the present invention.

FIG. 5 is an end perspective view of another exemplary tip according to embodiments of the present invention.

FIG. 6 is an exploded view of the tip of FIG. 5.

FIG. 17A is an enlarged partial top view of another embodiment of surgical tool with a tip suitable for cataract surgeries according to embodiments of the present invention.

FIG. 17B is an enlarged top view of the device shown in FIG. 17A, illustrating the door extended to occlude the aspiration port according to embodiments of the present invention.

FIGS. 18A-18C are side partial views of the tip of the device shown in FIGS. 17A and 17B shown with the door in a series of different configurations according to embodiments of the present invention.

FIG. 20A is a side perspective end view of a tip according to some embodiments of the present invention.

FIG. 20B is a side perspective partial cutaway view of the device shown in FIG. 20A.

FIG. 20C is a side perspective partial cutaway view of the device shown in FIG. 20A.

FIG. 20D is a front side perspective view of the device shown in FIG. 20A.

FIG. 20E is an exploded view of the device shown in FIG. 20A.

FIG. 20F is a side end perspective view opposite that shown in FIG. 20D.

FIG. 20G is a top perspective view of the device shown in FIG. 20A.

FIG. 21A is an exploded perspective view of another embodiment of a tip according to embodiments of the present invention.

FIG. 21B is a side perspective view of a primary body of the tip shown in FIG. 21A.

FIG. 21C is a partial assembly view of the device shown in FIG. 21A illustrating the side panels assembled to the primary body.

FIG. 21D is a partial assembly view of the device shown in FIG. 21A illustrating the side panels and door with door extension attached to the primary body.

FIG. 21E is a partial assembly side view of the device shown in FIG. 21A illustrating the outer top panel attached to the other components shown in FIG. 21D.

FIG. 21F is an assembled view of the device shown in FIG. 21A and also illustrates an optional textured surface according to embodiments of the present invention.

FIG. 21G is a partial section view of the assembled device shown in FIG. 21F.

FIG. 21H is a front, side perspective view of the assembled device shown in FIG. 21F illustrating the door "open".

FIG. 21I is a front, side perspective view of the assembled device shown in FIG. 21F illustrating the door closed.

DESCRIPTION OF EMBODIMENTS OF THE INVENTION

Figure 7:
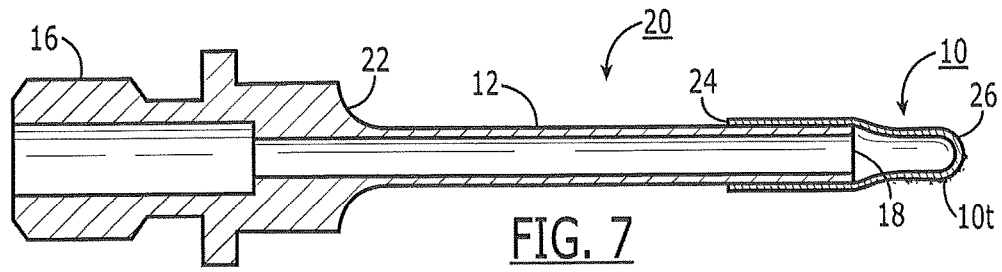
FIG. 7 is a section view of the tip of FIG. 5.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise.

The terminology used herein is for the purpose of describing particular embodiments only and is not intended to be limiting of the invention. As used herein, the singular forms, "an", "an" and "the" are intended to include the plural forms as well, unless the context clearly indicates otherwise. It will be further understood that the terms "comprises," "comprising," "includes," and/or "including" when used in this specification, specify the presence of stated features, regions, steps, operations, elements, and/or components, but do not preclude the presence or addition of one or more other features, regions, steps, operations, elements, components, and/or groups thereof.

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein.

Referring now to the figures, FIG. 1 illustrates a surgical device 20 with a tip 10 having a textured surface 10t. Unlike the MicroSmooth® polymer tips from Alcon, Inc., the tip 10 which, in some embodiments, is configured to be placed in a capsule bag of an eye of a patient during surgery (FIG. 4), has a small sub-portion ("patch") with a textured surface 10t.

The term "textured" refers to a surface that has a different surface finish or tactile surface pattern relative to smooth surfaces to provide a surface with increased grip and/or friction suitable for acting as an eraser on cortical fibers and/or for polishing the capsule bag, e.g., a "low friction" surface. The textured surface can be substantially smooth but have increased friction or grip relative to non-textured (smooth) finish surfaces. The texture can be similar to the microetched portion on a Kratz capsule polisher such as the BD Visitec™ capsule polisher from Beaver-Visitec International.

The term "tip" refers to a distal end portion of a tool for cortical clean up and/or polishing of the capsule bag. The term "patch" refers to a small localized exterior textured surface region that is integral to the tip body, typically having a size that is less than 50% of a surface area of the tip body. Thus, the word "patch" refers to a size of the textured surface which can be formed directly into the surface of the tip body as will be discussed below and does not require, but can include, a separate element to provide the textured surface.

The word "about" means that the size or amount referred to can vary from the particular amount, typically by +/−10%.

The term "phacoemulsification" (also referred to as "phaco") refers to both ultrasound and laser-based emulsification procedures used to disintegrate target interior eye tissue, typically the lens, for cataract surgery, as well as combinations of ultrasound and laser procedures. The term "electrical lead" refers to all electrical transmission paths including integrated conductive films, traces, filars, and cables.

The textured surface 10t can be provided on a sub-portion of the exterior surface of a single-use (disposable) elastomeric end cap 26 as shown in FIGS. 1-9 that is attached to a an aspiration cannula that defines the aspiration channel. The tip 10 can include at least one aspiration aperture 30 on an end portion thereof, typically a single aspiration aperture 30. The end cap 26 can comprise a monolithic material such as an elastomer or polymer including, but not limited to, silicone rubber.

In some embodiments, the surgical device 20 with the multifunctional tip 10 can be used for ultrasound phacoemulsifcation procedures. In other embodiments, the tip 10 can be used for laser-phaco cataract procedures such as after or during femtosecond laser treatment to remove nuclear fragments and epinucleus. The tip 10 can provide irrigation and/or aspiration. In some embodiments, such as where used in lieu of ultrasound phaco, the tip 10 but may include a larger aspiration port 30 to accommodate the larger fragments (see, e.g., FIGS. 14A-C, FIGS. 15A-D).

FIGS. 1-3 show the device 20 as including an irrigation sleeve 24 that is separate from the end cap 26. In this embodiment, irrigant can flow between the cannula 12 and the sleeve 24. The end cap 26 can include a flange 26f that is rearward of the aspiration port 30 and the textured patch 10t. The cap 26 can have a smooth surface 10s about the aspiration port 30 and rearward thereof as shown in FIGS. 1-3, for example. The textured surface 10t can be spaced apart between about 0.1 mm to about 5 mm from the aspiration port 30 and other than the textured patch 10t, the tip 10 can have a smooth outer surface. The textured patch 10t can reside only on the tapered distal most end of the tip or end cap so that the texture terminates proximate a junction that merges into the smooth vertical outerwalls. This textured patch 10t can occupy a small length of the distal end of the tip 10 and/or end cap 26, similar to an eraser on a pencil. This small length can be between about 0.1 mm to about 3 mm.

Figure 8:
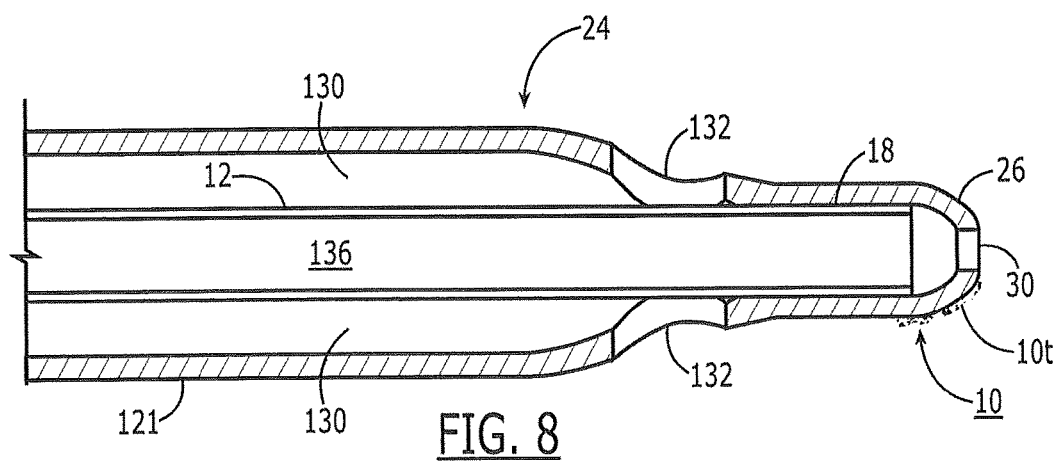
FIG. 8 is an enlarged partial section view of another exemplary aspiration tip according to embodiments of the present invention.

FIGS. 5-7 show a sleeve 24 that attaches to an outer surface of the cannula 12 without leaving an annular space for irrigant. FIG. 5 shows that the end cap 26 can be integral to the sleeve 24. FIG. 8 also shows that the end cap 26 can be integral to the sleeve 24 with the sleeve 24 configured to define a flow channel 130 and irrigation port(s) 132 and attach to the aspiration cannula 12. The tip 10 and/or end cap 26 can have a very small width, such as less than about 2 mm, including about 0.9 mm and about 1.1 mm, for example.

Referring to FIG. 4, the tool 20 can releasably connect, via a hub 16, to an aspiration 100 and/or irrigation system 110 with a hand piece 100h as is well known to those of skill in the art. The cannula 12 can be open at distal end 18 and can be attached to hub 16 at proximal end 22. The tool 20 may also optionally be in communication with an ultrasound source 300 and may include an electrical lead 31 that extends to the tip 10.

As shown in FIGS. 1-3, the textured surface 10t can cover only the distal end of the tip 10 and typically terminates prior to the aspiration port(s) 30 so that the remainder of the tip 10, end cap 26 or sleeve 24 is smooth 10s.

Figure 9:
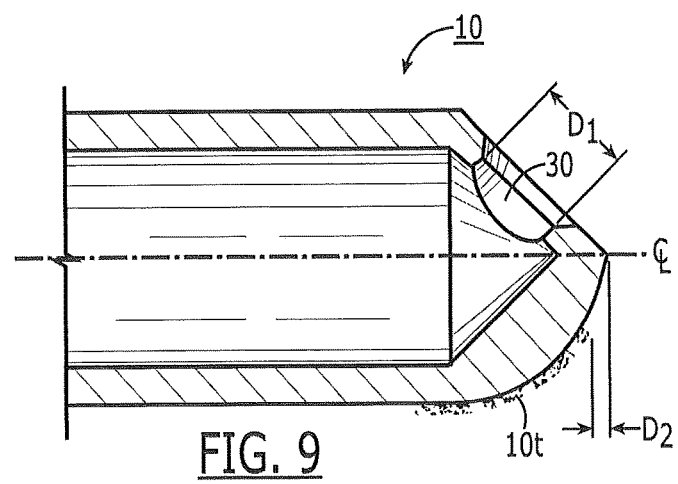
FIG. 9 is an enlarged partial section view of a distal end portion of another tip configuration according to embodiments of the present invention.
Figure 13A:
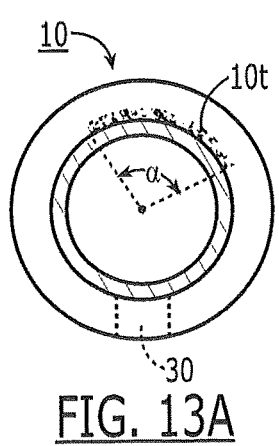
FIGS. 13A and 13B are cross-sectional views taken along line 13-13 in FIG. 12 illustrating that the textured surfaces can be provided as a subset of a distal end, covering a portion of a perimeter (e.g., a circumference) of the sleeve/tip according to embodiments of the present invention.
Figure 13B:
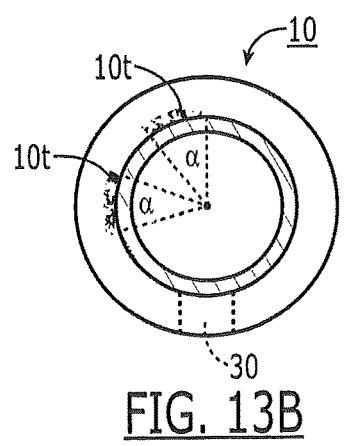

In some embodiments, the textured surface 10t can reside on an opposite surface from an irrigation/aspiration port 30 (FIGS. 9, 13A, 13B). The textured patch region 10t can have a length "L" that is recessed axially inward a distance from the distal tip end and that terminates away from the proximal end of the tip that is attached to the tool body (FIGS. 5, 9).

In the embodiment shown in FIG. 8, the distal end 18 of cannula 12 is sealed by a reduced diameter portion of the sleeve 24, which is typically integrally formed at the distal end of shaft 121. The sleeve 24 is generally tubular in shape and closed on its distal end except for aperture 20. The reduced diameter of the sleeve 24 is configured to seal tightly about the distal end portion 18 of cannula 12. The sleeve 24 is also configured to form a coaxial gap 130 around cannula 12. Gap 130 allows irrigation flow down gap 130 and out ports 132. When vacuum is applied to interior lumen 136 of cannula 12, material can be aspirated through port 30, down interior lumen 136 and out of the tool 20.

FIGS. 1-3, 5 and 9 show the aperture 30 spaced away from the distal end of the tip 10 while FIG. 8 shows that the aperture 30 can reside on the distal end of the tip 26.

FIG. 9 shows the aperture 30 on an end of the tip but offset from a centerline of the end cap 26 and/or tip 10. FIG. 9 also shows the textured surface 10t on a rounded portion to terminate prior to an edge adjacent a planar surface holding the aperture 30. The aperture 30 can have a size D1.

The textured surface 10t can be configured to occupy or reside on less than the entire end of the tip. The textured surface 10t can be recessed or offset a distance from the distal end of the tip, such as a distance "D2" as shown, for example, in FIG. 9. The distance "D2" can be between about 0.1 mm to about 10 mm, typically between about 1 mm to about 3 mm.

Figure 10A:
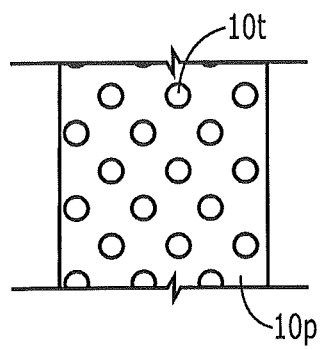
FIGS. 10A-10E are partial cutaway views of examples of textured surfaces according to embodiments of the present invention.
Figure 10B:
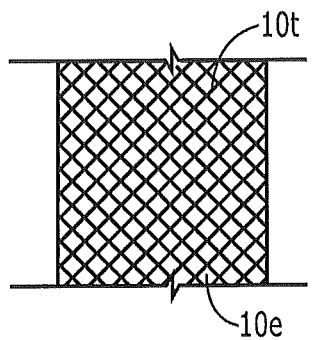
Figure 10C:
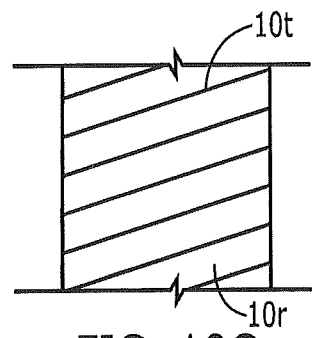
Figure 10D:
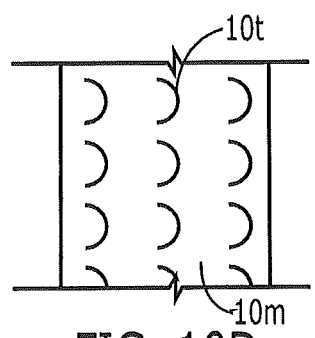
Figure 10E:
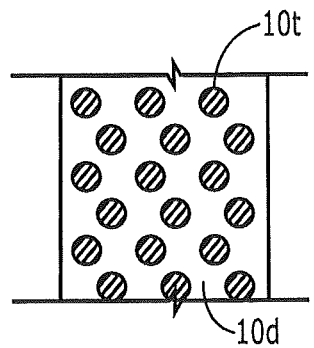
Figure 11:
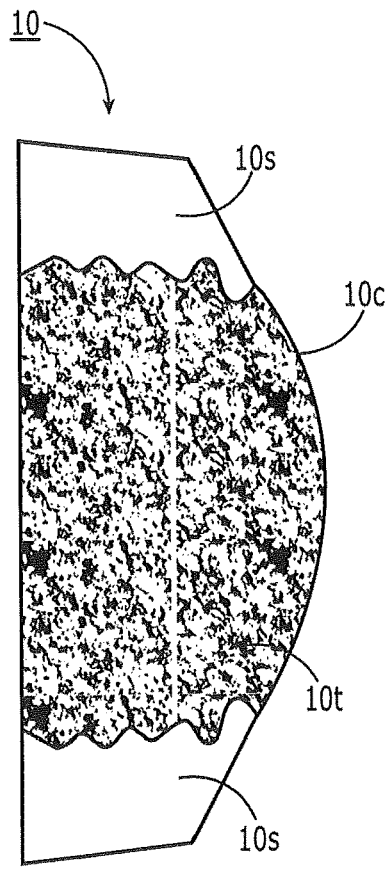
FIG. 11 is an enlarged partial section view of a portion of a tip with a textured surface according to embodiments of the present invention.

FIGS. 10A-10E and 11 illustrate examples of different textured surface 10t configurations. FIG. 10A illustrates the textured surface 10t includes particulates such as nanoparticles or granular material as a surface coating. FIG. 10B illustrates an embossed surface 10e. The embossed surface can be in a regularly or irregularly repeating fashion of one or more defined shapes. Although shown as a generally diamond shaped pattern, other shapes may be used including honeycomb, polygons, circles, or other shapes. FIG. 10C illustrates a slightly roughened surface 10r, FIG. 10C illustrates the textured surface can include mounds while FIG. 10D illustrates dimples. Combinations of projections and recessions, e.g., mounds and dimples, can also be used. FIG. 11 illustrates a cluster 10c of irregular features on an exterior surface of the tip 10. FIG. 11 also illustrates that the tip can include a smooth surface 10s adjacent the textured surface 10t. Combinations of the above or other textures or patterns may be used.

FIG. 10 illustrates that the tip 10 can include the textured surface 10t on an elongate segment of the sleeve 24 which can be on one side of the tip 10, typically terminating proximate to the port 30 but can extend a distance rearward from the port 30, such as between about 0.1 mm to about 5 mm, and in some embodiments between about 1 mm to about 5 mm.

Figure 12:
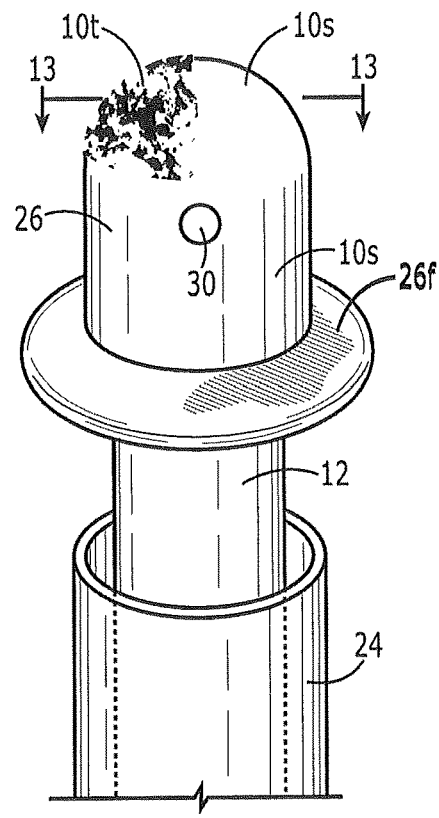
FIG. 12 is an enlarged partial view of a device with an aspiration tip according to embodiments of the present invention.

In some embodiments, the textured surface 10t can reside over a sub-portion portion of a perimeter region of the tip 10 as shown in FIGS. 12, 13A and 13B. FIGS. 13A and 13B illustrate that the textured surface 10t can reside or extend over less than about half the perimeter (which may be a circumference) of the tip 10. The textured surface 10 can be provided as a narrow patch segment on the tip 10, such as between about 10% to about 30% of the circumference or other perimeter shape. FIG. 12 illustrates that the textured patch can reside over less than an entire distal end surface, typically so as to cover less than about 50% thereof. FIGS. 13A and 13B are exemplary section illustrations of the tip 10 taken along lines 13-13 in FIG. 12. FIGS. 13A and 13B illustrate that the textured surface 10t can reside over less than about 90 degrees of the circumference of the tip 10. FIG. 13B illustrates that the textured surface 10t can be discontinuous about the perimeter. The textured surface 10t can occupy less than half a surface area of the perimeter of the distal end portion of the tip 10 or sleeve. In some embodiments, the textured surface 10t can be provided as a narrow strip or patch on the distal end portion of the tip. In some embodiments, the textured surface 10t can reside about a defined angle "α" that is typically less than 180 degrees, such as between about 15 degrees to about 120 degrees, such as about 30 degrees, about 45 degrees, about 60 degrees, about 75 degrees, about 90 degrees, about 110 degrees, for example. FIG. 13B illustrates two spaced apart textured segments 10t can be used although more than two, such as between 2-10 segments or more can be used. The segments can have the same or different angular coverage "α".

Some of the textured surface patch configurations may allow a surgeon to rotate the tip 10 to enter the capsule so that the tip 10 contacts the capsule with a smooth surface during insertion (or retraction). The surgeon can then rotate the tip 10 to erase cortical fibers and/or polish the capsule and/or remove nuclear fragments using the textured surface 10t. The partial textured surface 10t can be provided with a color contrast to other portions of the tip to allow for ease of viewing during a surgical procedure.

The textured surface 10t of the tip can be formed or provided in any suitable manner. For example, coating the sleeve using a biocompatible coating, such as a coating with particulates, dipping the sleeve in an acid rinse or ultrasonic bath (for pitting), embossing the sleeve, or molding the sleeve in a mold which provides the desired surface texture or attaching a small separate patch material onto a portion of the outer surface of the tip. In some embodiments, the textured surface of the sleeve 24 can be rough but without jagged edges that might tear the capsule bag. The roughened textured surface 10t may be formed in any suitable manner such as sandblasting, pinging, rubbing against a rough tool or sand paper and the like.

Figure 14A:
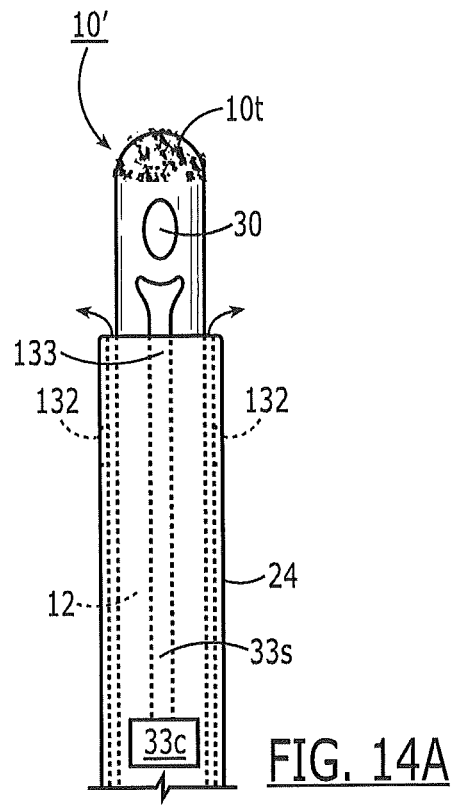
FIG. 14A is an enlarged partial cutaway view of another embodiment of surgical tool with a tip suitable for cataract surgeries according to embodiments of the present invention.
Figure 14B:
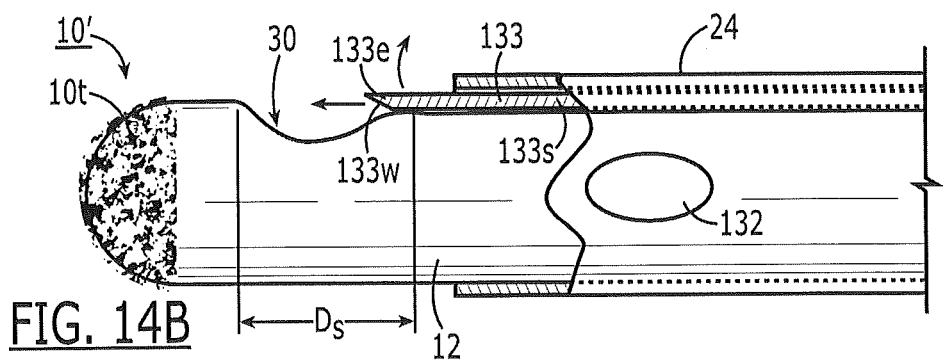
FIG. 14B is a side cutaway view of the device shown in FIG. 14A, illustrating an open aspiration port according to embodiments of the present invention.
Figure 14C:
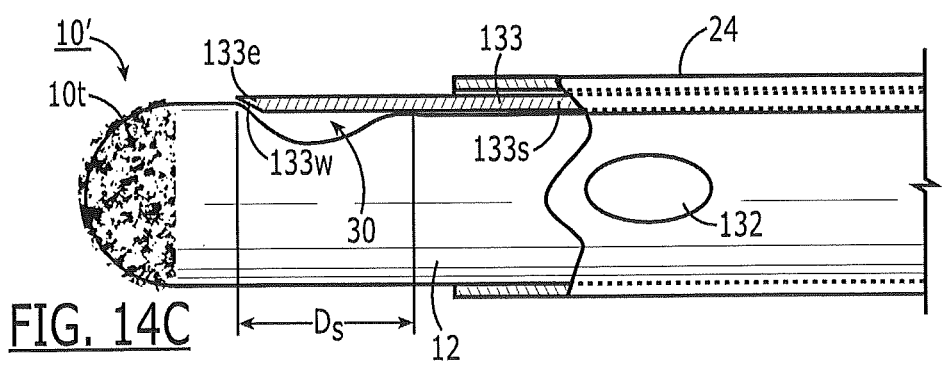
FIG. 14C is a side cutaway view of the device shown in FIG. 14A, illustrating a partially closed aspiration port according to embodiments of the present invention.

FIGS. 14A-C illustrate another embodiment of the surgical device 20 with a 10'. The tip 10' can include the textured tip 10t as described above for polishing and also or alternatively can include a cortex/lens removal system with a longitudinally translatable member 133 that can move between distal and proximal directions. In operation, lens fragments, especially nucleus or cortex fragments try to be aspirated via port 30, but larger ones can get stuck. The translating member 133 can be configured to have an oscillating and/or reciprocating movement to "chop", fragment, crush or otherwise reduce the larger lens fragments in size (those that are trying to be aspirated via the port 30 but are too large) with the forward/aft oscillating and/or reciprocal movement of the translating member 133. To be clear, although shown with a textured tip 10t, in some embodiments, the device 10' can be configured without the textured tip 10t.

The stroke "Ds" of the translating member 133 during the oscillation/reciprocal movement can be very short, e.g., the forwardmost position can terminate proximate the leading end of the aspiration port 30. The stroke distance can be limited and controlled and can be between about 2 mm to about 0.1 mm, typically between about 2 mm to about 0.5 mm. The stroke cycle can be rapid or slow, typically between 1-10 Hz. The cycle speed and distance may be adjustable or selectable from a predefined operational list that programmatically controls the movement upon activation of a control 33c by a user. The control 33c can comprise a user-actuated control in communication with the shaft 133s, such as manual control of any suitable type, including, for example, a switch, button, thumbwheel, foot pedal or may comprise an electronic control such as a voice activated control.

The user-actuation control 33c is configured to control the reciprocating movement and/or oscillation of the translating member 133, e.g., a finger press on the shaft or foot pedal position. The control 33c can allow open/oscillating/closed, just oscillating, or oscillating and closed action of the member 133. Separate controls may also be used for the different actions.

The aspiration port 30 can be sized to be able to engulf lens fragments. The ones that fit in the port 30 can simply be aspirated, but the larger ones that get stuck can then be "chopped", fragmented or otherwise reduced in size with the extension and/or reciprocal movement of the translating member 133. The port 30 can have a size that is about 1-3 mm in diameter. Non-circular irrigation port shapes may also be used and the port 30 can have a width and length that is between 1-3 mm.

As shown, the sleeve 24 can also have at least one irrigation port 132, typically two ports, one on each lateral side of the translating member 133.

The leading edge of the translating member 133e can have a wedge configuration to trap lens fragments. As shown, the wedge 133w can angle down with a longer end being above a lower shorter end.

The shaft 133s can slidably reside in a suitable and/or correspondingly shaped (mating) groove, slot or channel 122 in the outer wall of the cannula 12 (or inner wall of the sleeve 24) for alignment and orientation control (e.g., similar to a "tongue and groove" or rail configuration). The groove 122 can extend down the center of the device 20. The translating member 133 can be extended when the fragmenting is complete to aspirate via a small gap space left between the end of the translating member 133e and the underlying partially closed aspiration port 30 (FIG. 14C). The tip 10t can then be used to polish the capsule. The device can be configured to complete the procedure after the laser has done its part in dismantling the lens. Preferably, no ultrasound is required for the procedure (a safe and cost effective solution to avoid ultrasound).

FIGS. 15A-15D illustrate a similar configuration as the embodiment shown with respect to FIGS. 14A-14C. In this embodiment, the aspiration port 30 can have two segments, a "large" size segment 33L and a small size segment 33s. Like before, the translating member 133 can reside in a groove 122 (e.g., channel or recess) on an outer surface of the cannula 12 or on an inner surface of the sleeve 24 (or combinations thereof). The groove 122 can extend down the center of the device 10'. The translating member 133 can translate forward and aft to perform the lens crushing and, when desired, close the larger port 33L.

The aspiration port 30 can have an irregular shape such as a "keyhole" shape 30k (FIG. 15A) with the larger and smaller segments 33L, 33s. In other embodiments, two separate adjacent ports can be provided, one smaller than another (not shown). The smaller port or port segment 33s can have a diameter of about 0.25 mm to about 0.5 mm. The larger port or port segment 33L can be 2 times to ten times larger than the smaller port or port segment 33s.

The leading end 133e of the translating member can have a shape that substantially corresponds to a shape of the larger segment of the port 33L so as to occlude the underlying portion of the port 30, e.g., larger segment 33L. As shown, the leading end 133e has a circular shape with a tapered or wedge shaped end that can trap lens fragments over the port 30. The leading end of the groove 122 can have a correspondingly shaped, closed surface recess 122e. As shown, the recess 122e is wider than the long recess of the shaft 122s and terminates proximate the port 30.

The larger section or larger port 33L can reside a further distance away from the distal tip of the device 10t relative to the small portion 33s. The larger segment of the port or larger port 33L is sized to be able to engulf lens fragments. The lens fragments that fit in port 33L can simply be aspirated, but the larger ones that get stuck can then be "chopped", fragmented, crushed or otherwise reduced in size with the extension and/or reciprocal movement of the translating member 133.

Figure 15A:
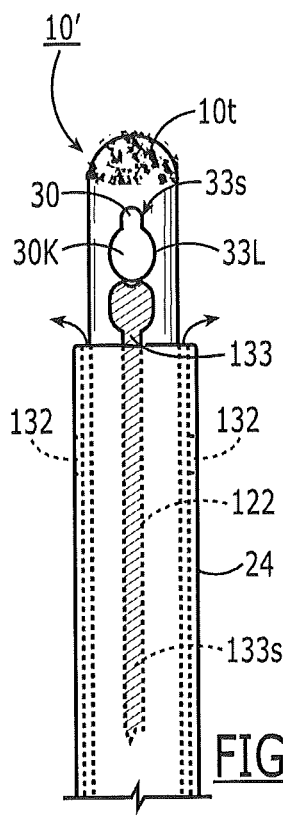
FIG. 15A is an enlarged partial cutaway view of another embodiment of surgical tool with a tip suitable for cataract surgeries according to embodiments of the present invention, illustrating a translating member and open aspiration port according to embodiments of the present invention.
Figure 15B:
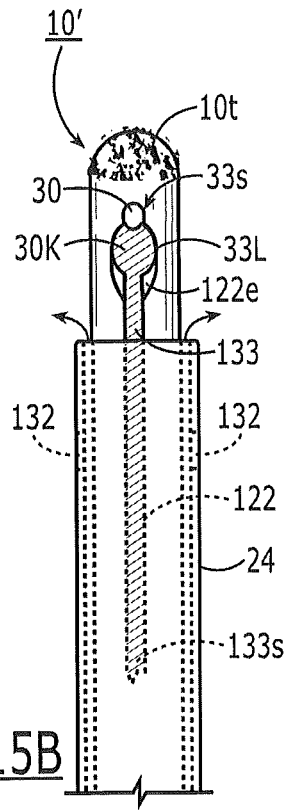
FIG. 15B is an enlarged partial cutaway view of the tool shown in FIG. 15A illustrating the translating member and a partially closed aspiration port according to embodiments of the present invention.
Figure 15C:
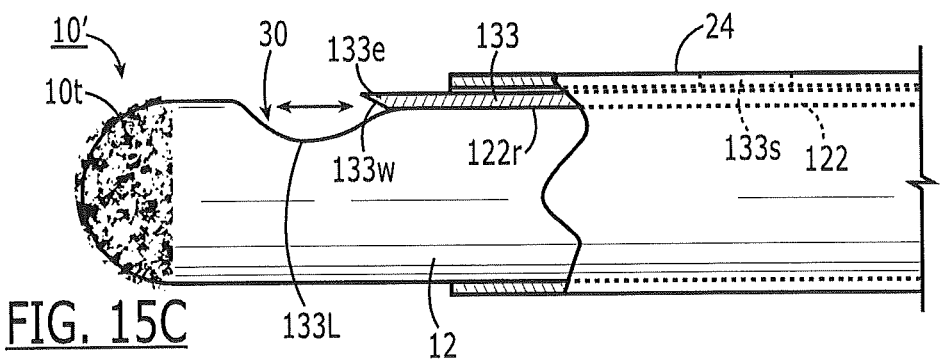
FIG. 15C is a side cutaway view of the device shown in FIG. 15A, illustrating an open aspiration port according to embodiments of the present invention.
Figure 15D:
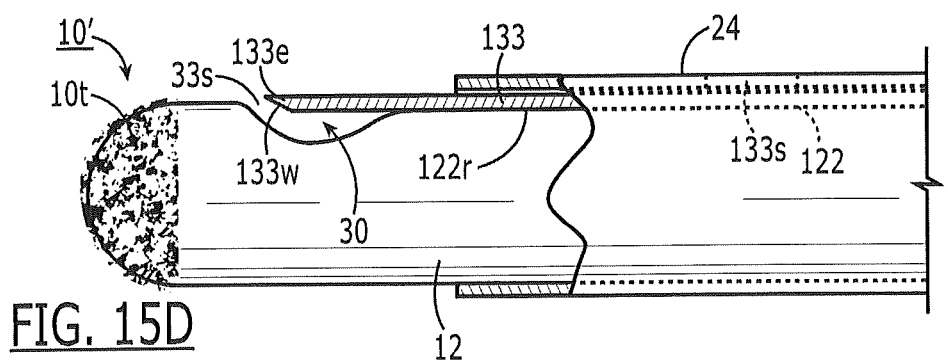
FIG. 15D is a side cutaway view of the device shown in FIG. 15A, illustrating a partially closed aspiration port according to embodiments of the present invention.

FIGS. 15C and 15D illustrate, in side view, the movement of the translating member 133, e.g., forward and aft movement, to fragment, crush or otherwise act on the lens fragments, when needed. Once the lens is fully removed, the translating member 133 can be positioned to cover the larger port 33L, e.g., the bottom of the keyhole 30k, leaving the smaller port 33s (e.g., a top of the keyhole) to aspirate the cortex safely. The tip 10t can then be used to polish the capsule. This should be all that is required after the laser has done its part in dismantling the lens. Preferably, no ultrasound is required for the procedure (a safe and cost effective solution to avoid ultrasound).

Figure 16A:
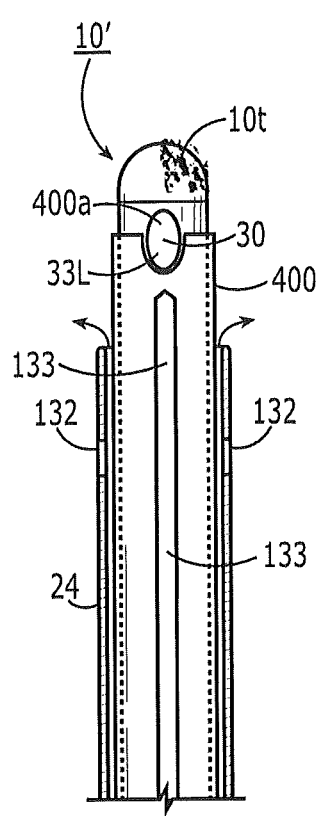
FIG. 16A is an enlarged partial cutaway view of another embodiment of surgical tool with a tip suitable for cataract surgeries according to embodiments of the present invention.
Figure 16B:
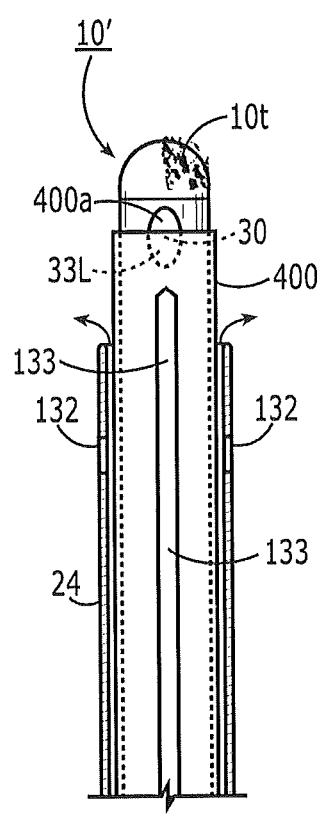
FIG. 16B is an enlarged partial cutaway view of the device shown in FIG. 16A, illustrating a sleeve rotated to partially occlude the aspiration port according to embodiments of the present invention.

FIGS. 16A and 16B illustrate an alternate embodiment where the device 20 can include a thin rotatable sleeve 400 that resides over the cannula 12 and under the translating member 133 and has a wall with a large aperture 40a allowing exposure of the port 30 and at least one laterally spaced apart small aperture 400s. When rotated so that the small aperture 400s overlays the port 30, the sleeve 400 can partially close the port 30 and provide the small access port segment 33s. Thus, in this embodiment, the translating member 133 is not required to close against the port 30 to form the small port 33s as the sleeve 400 cooperates with the tip 10 to aspirate fragmented lens after the oscillation/reciprocal action of the leading end of the translating member 133. Again, the device 20' can include a user-actuated control 33c that is in communication with the shaft 12s for controlling the reciprocating movement or oscillation of the translating member 133, The device 20 with the tip 10, 10' may be particularly suitable for laser-phaco. In the past, sometimes when a small nuclear piece is left behind and noticed during cortex removal, a second instrument is used to smash it into the tip while aspirating. The tool with the multi-functional tip having the translating member 133 with an optional textured external surface 10t can avoid the need for such a second device and/or ultrasound phaco.

FIGS. 17A, 17B and 18A-18C illustrate embodiments of the device 20 which has a tip 10" that can have an open leading end 10l and a translatable forward segment or door 235. The open leading end 10l can be configured with a wall 10w that slants or tapers downward at an angle that is less than 90 degrees, typically between about 15 degrees and about 60 degrees, such as about 15 degrees, about 20 degrees, about 25 degrees, about 30 degrees, about 35 degrees, about 40 degrees, about 45 degrees, about 50 degrees, about 55 degrees and about 60 degrees. The leading end can be configured to place one perimeter edge at a forwardmost position, labeled as a bottom 10b, so that this portion is more forward or distal relative to the wall on an opposing side of the lumen (shown as the upper side in these figures), which can define a lumen for a relatively large aspiration port 230. The port 230 can be sized and configured with a size sufficient to extend above and below the centerline of the aspiration lumen 136. In some embodiments, the size of the (large) aspiration port 230 can be between about 1 mm to about 1.5 mm across and between about 0.75 mm to about 1 mm in height, typically about 1.5 mm×about 1.0 mm.

The leading end 10l can alternatively be configured with other shapes, such as that shown in FIGS. 8 and 9. The leading end 10l can place the port 230 above a centerline as shown in FIG. 9 (as port 30). Thus, the door 235 can extend down to totally or partially close the port 30 of FIG. 9 or FIG. 8, for example.

The translating forward segment or door 235 can have an extension or shaft 133s that translates the forward segment or door 235 to close the open port 230 as shown in FIGS. 17B, 18B and 18C. The door 235 can act to "chop" cortex tissue to facilitate aspiration removal. The door 235 can reciprocate to help chop the tissue similar to some of the embodiments discussed above. The door 235 can be configured to have an oscillating and/or reciprocating movement to "chop", fragment, crush or otherwise reduce the larger lens fragments in size with the forward/aft oscillating and/or reciprocal movement of thereof. The stroke "Ds" of the door 235 during the oscillation/reciprocal movement can be short, e.g., the forwardmost position can terminate proximate the leading end of the aspiration port 30. The stroke distance can be limited and controlled. The stroke distance of the door may be between about 2 mm to about 0, 1 mm, typically between about 2 mm to about 0.5 mm. The stroke cycle can be rapid or slow, typically between 1-10 Hz. The cycle speed and distance may be adjustable or selectable from a predefined operational list that programmatically controls the movement upon activation of a control 238 by a user. The control 238 can comprise a user-actuated control in communication with the shaft 133s (and/or extension 435), such as manual control of any suitable type, including, for example, a switch, button, thumbwheel, foot pedal or may comprise an electronic control such as a voice activated control.

The door 235 of the tip 10" can allow large cataract fragments to be more directly approached, similar to current phaco tips. In operation, large pieces that may get stuck can be chopped by the door 235 that translates or rolls down to substantially, if not totally, completely cover/close the opening 230 of the tip 10t. The door 235 can be configured to partially or totally occlude the large aspiration port 230. The door 235 can be configured to travel forward and downward between fully or partially retracted and fully or partially extended positions over the open port 230 or 30 (FIGS. 8, 9) on the leading end of the tip 10". The port 230 can be axially and/or longitudinally in-line with the aspiration lumen or channel 136. The port 230 can have a center that is concentric with an axially extending center line of the longitudinally extending aspiration lumen or channel. The port 230 may have substantially the same size as the aspiration lumen or channel 136 or may be smaller.

The door 235 can be operated either manually by the surgeon's finger(s) and/or electronically using an electric, pneumatic or hydraulic actuator. As shown, the device 20 can include an external user input 238 that is attached to the shaft 133s to move the door 235.

The door 235 can translate forward and down to close over the open port 230. The reference to the "down" movement is with respect to the orientation of the device 20 shown in FIGS. 17A, 17B and 18A-18C. Thus, the door 235 can move forward and upward if oriented in the reverse (or to the side and inward if oriented in a side orientation).

Figure 19A:
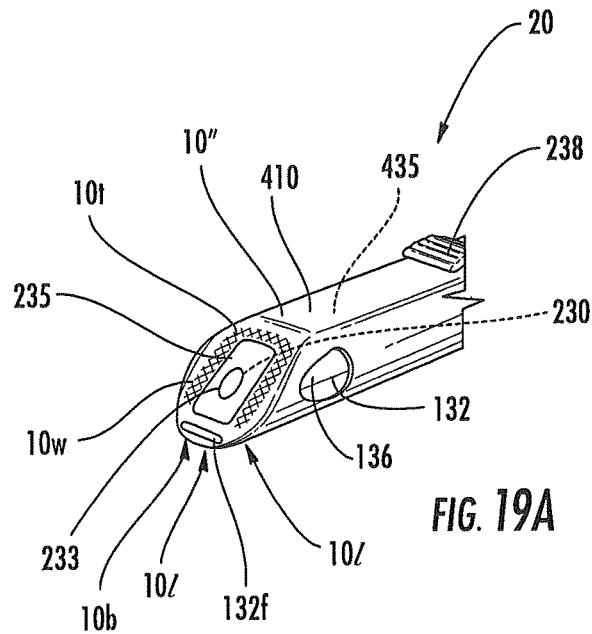
FIGS. 19A-D are front side perspective views of tips of surgical tools suitable for cataract surgeries according to embodiments of the present invention.
Figure 19B:
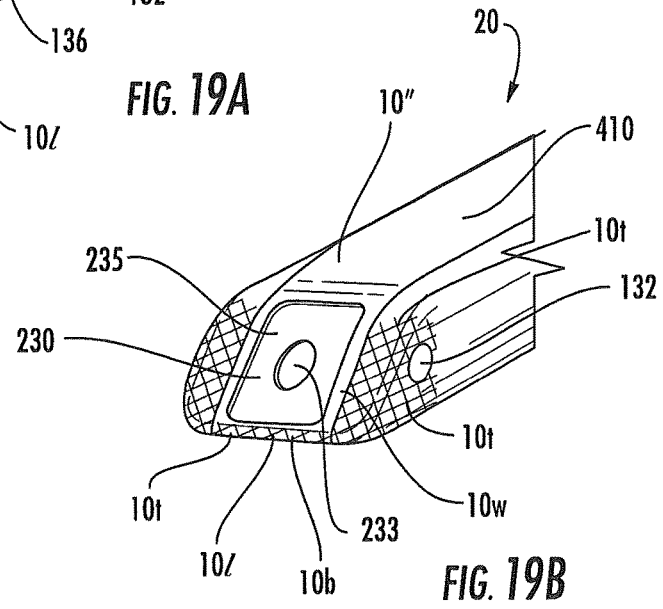
Figure 19C:
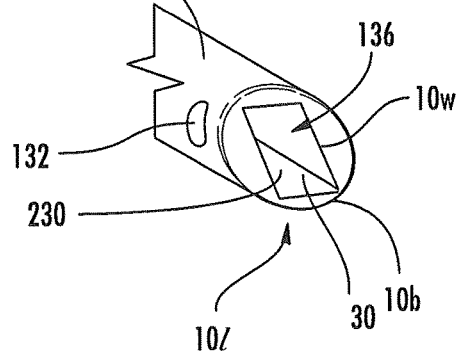
Figure 19D:
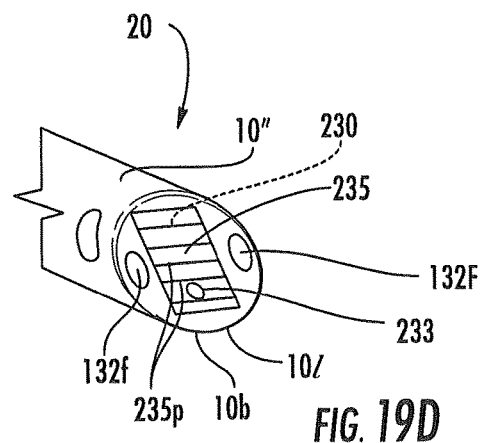

The shape of the leading end 10l, when viewed from the front, can be circular, oval, rectangular, or curvilinear. When viewed from the side, the leading end 10l can be angled or tapered. The forwardmost portion of the open leading end, labeled as a bottom 10b in the orientation in some of the figures, can be above the bottom and/or may be curved upward (FIGS. 8, 9, 19A, 19C, 19D) or planar (FIG. 19B). The open leading end 10l can define the primary aspiration port 230 and/or 30 (FIGS. 8, 9, 36) and the primary aspiration port may extend across at least 30% of the length and/or height dimension of the leading end of the tip 10l, typically it extends across a major length and/or height dimension of the leading end of the tip and can aspirate in-line with the aspiration lumen or channel 136.

In some embodiments, the tool tip 10" is configured as an irrigation and aspiration device. Thus, in some embodiments, the tip 10" can include at least one irrigation port 132 (e.g., FIGS. 19A, 19B). The at least one irrigation port 132 can be a plurality of spaced apart ports 132. The irrigation ports 132 can have a larger cross-sectional size than the fine or smaller aspiration port 233, and typically are between about 0.3 mm to about 0.9 mm in cross-sectional size (height and/or width), more typically between about 0.7 mm to about 0.9 mm for suitable fluid flow. However, other sizes may be used.

In some embodiments, the tip 10" (or any of the other tips 10, 10' described hereinabove), can include a front irrigation port 132f as shown, for example, in FIGS. 20A-20G. These fluid irrigation ports 132f can function as "water jets" to facilitate cortex removal.

In some embodiments, one or more of the ports 132 may be configured for substantially coaxial or substantially aligned aspiration and irrigation on a substantially common axis.

In other embodiments, the tool 20 can be used with a separate irrigation tool for a "bimanual" configuration.

In some embodiments, the tool tip 10" is configured as an aspiration only device and does not include an irrigation port.

In other embodiments, the tool tip 10" is configured as an irrigation/aspiration and polishing device.

The door 235 and adjacent frame or wall 10w surrounding the door outer perimeter, can have a perimeter that is substantially polygonal (e.g., square or rectangular), circular, oblong, oval or other geometric shape.

The door 235 can comprise at least one small aspiration port 233. The small port 233 can have a cross-sectional width that is less than the large port 230, typically about 10-50% of the cross-sectional size of the larger port 230. In some embodiments, there is a single port 233 that is smaller in size than the larger port 230 which can reside at a substantially medial location in the door 235 (when closed) or may reside at bottom or bottom third of the door 235. The small port 233 can have a size that is between about 0.3 mm in width/height to about 0.6 mm width/height opening, typically about a 0.5 mm diameter opening. In some embodiments, at least one small port, is a single port that can reside in the center of the door 235, for fine or small aspiration of cortex.

Figure 22:
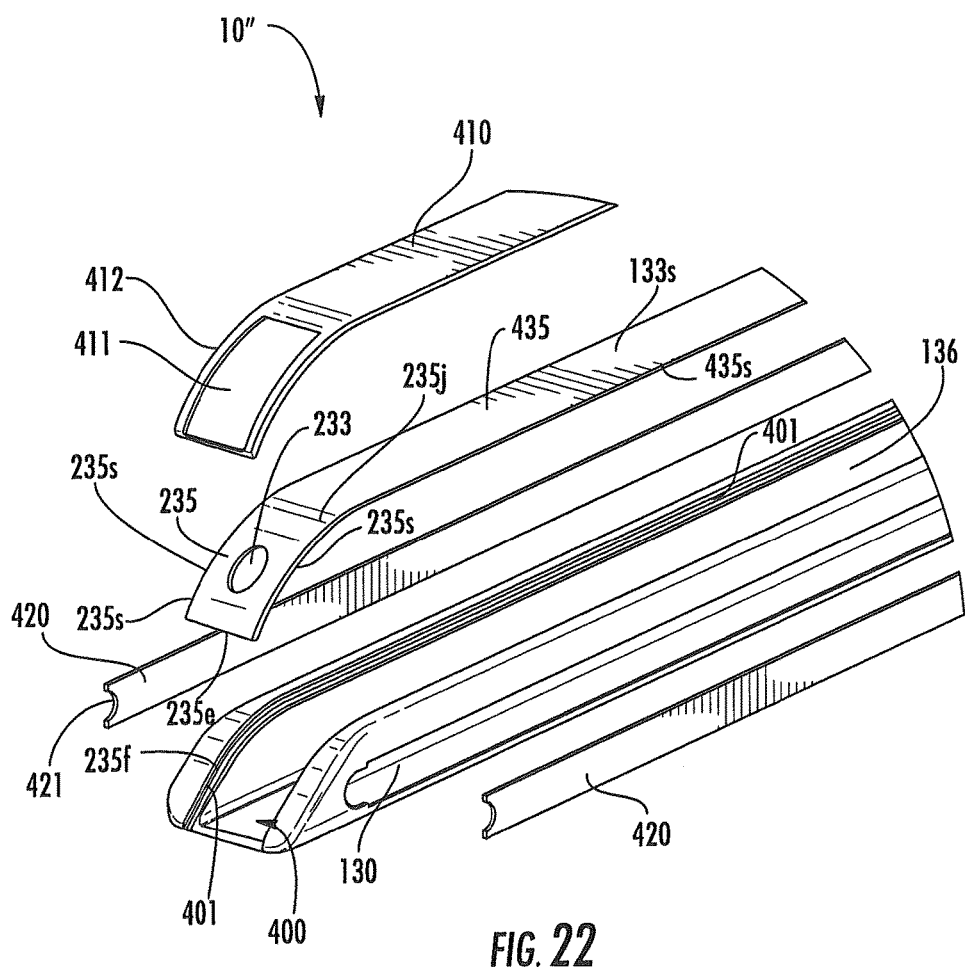
FIG. 22 is an enlarged exploded view of the device shown in FIG. 21A.
Figure 26:
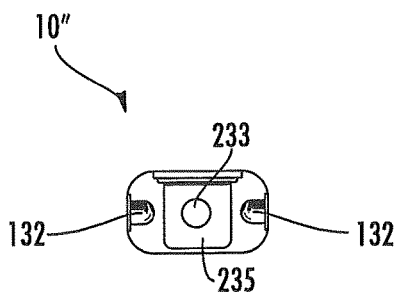
FIG. 26 is a leading end view of the device shown in FIG. 23.
Figure 23:
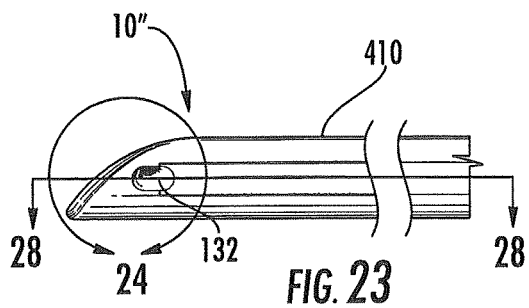
FIG. 23 is a side view of another embodiment of a tip according to embodiments of the present invention.
Figure 27:
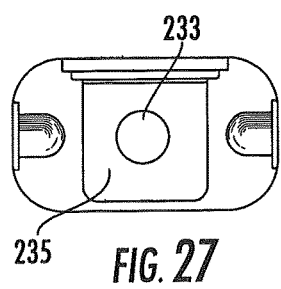
FIG. 27 is an enlarged end view of the device shown in FIG. 23.
Figure 29:
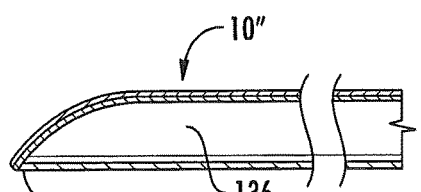
FIG. 29 is a section view taken along lines 29-29 in FIG. 25.
Figure 25:
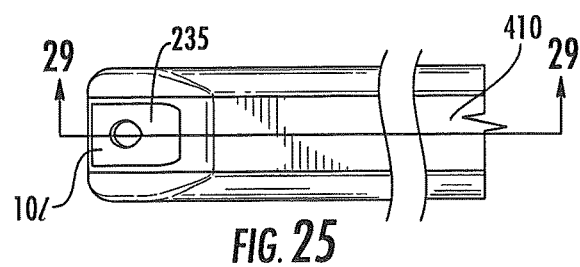
FIG. 25 is a top view of the device shown in FIG. 23.
Figure 24:
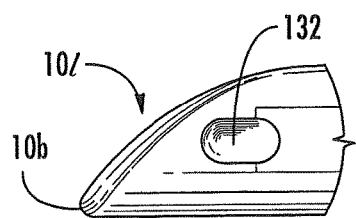
FIG. 24 is a partial, enlarged end view taken at detail "24" in FIG. 23.
Figure 28:
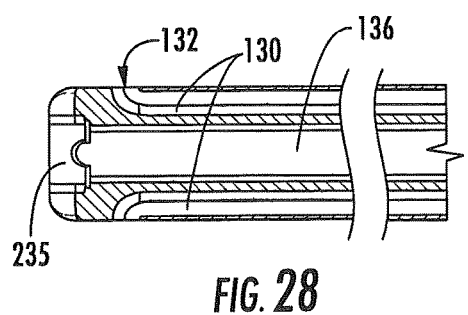
FIG. 28 is a section view of the device taken along lines 28-28 in FIG. 23.

The door 235 can be planar or slightly curved outwardly (FIGS. 18C, 19A, 19B, 19D) across the opening 230 when in the extended or forwardmost (closed) position and be curved or planar when in the retracted configuration (FIG. 17A, 18A, 22). The door 235 can be planar or curved when extended as shown in 18C, 20F, 21I, and 19D for example. The door 235 can articulate at a joint 235j (FIG. 22) relative to the shaft or extension or fold or bend as it is extended or retracted to be substantially planar and reside under a planar overlying outer cover 410 (FIGS. 19A, 19B).

In some embodiments, the door 235 can be flexible. In some embodiments, the door 235 can be rigid or semi-rigid. In some embodiments, the door 235 is metal. In some embodiments, the door 235 is flexible or semi-rigid and is polymeric.

In some embodiments, the door 235 is sized to have a width that is greater than the port 230.

As shown in FIGS. 20E, 21A and 22, in some embodiments, the outer edges of sides of the door 235s can be held in guides, channels or rails 401 to controllably extend and retract the door 235 over the open lumen 230. The tip 10" can be configured with guides, channels or rails 401 that hold the edges 235s as the door 235 is retracted and extended. The guides, channels or rails 401 can extend to trap the outer sides 435s of the extension or shaft 133s of the door as well (e.g., FIG. 22).

In some embodiments, the door 235 can be pulled shut as it is extended by use of a vacuum. The door 235 can include very small through-apertures (smaller than the small aspiration port(s) 233 that cooperate with the vacuum to control the suction force.

As shown in FIGS. 20A-G and 21A-I, in some embodiments, the door 235 can have a perimeter that is trapped in or by guides, channels or rails 401 on a wall of the tip 10", e.g., in a frame of the door 235f to force the door down in the guides, channels or rails 401 about a perimeter frame of the door 235f to control the movement and force the door to close across the lumen at the leading end of the tip 10".

In some embodiments, the door 235 can have articulating segments 235p (FIG. 19D), such as connected panels or planks which can be formed as discrete planks or panels attached together to close shut against each other or may be formed of a single piece of flexible material with preferentially scored or thinner sections. In some embodiments, the door 235 can comprise a shape memory alloy that takes on the curved downwardly extending closed shape as it is released from the retracted position.

The door leading end 235e can be configured to releasably lock with the "bottom" or "floor" 10b of the leading end of the tip 10" when closed. It is noted that the terms "floor" and "bottom" are used as a relative descriptive term for the orientation of the device 20 shown in FIGS. 17A-18C, 20, 21 and 22, for example. Thus, for example, and as noted above, the "floor" or bottom 10b can alternatively be a side or ceiling depending on the orientation. The forwardmost end of the door 235e, when in a closed lumen configuration, can reside abutting against an outer surface of the wall 10w thereat, flush with the wall 10w, or inside the wall in channels, guides or rails 401 (e.g., FIG. 21H) thereat.

In some embodiments, the door 235 in the closed position is not required to extend across or all the way down against the wall and can provide a smaller opening rather than close the entire lumen or large aspiration port 230.

Figure 33:
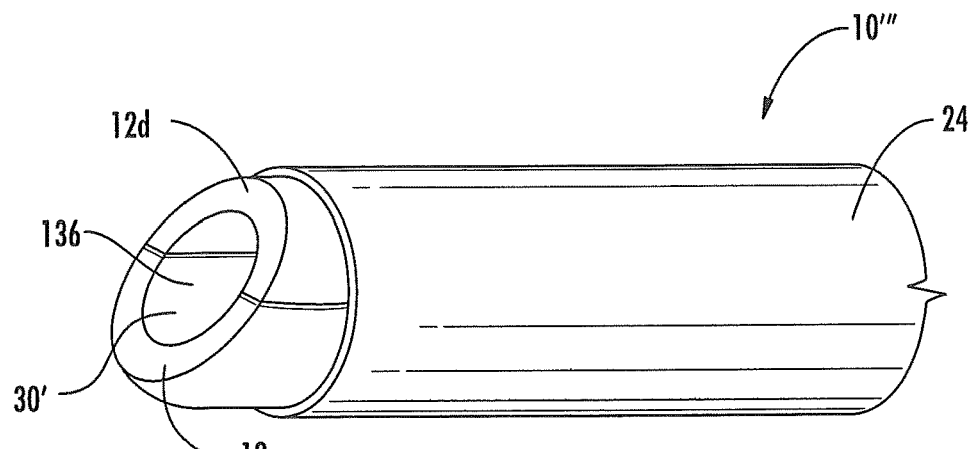
FIG. 33 is a partial end perspective view of another embodiment of the aspiration tip according to embodiments of the present invention.
Figure 34A:
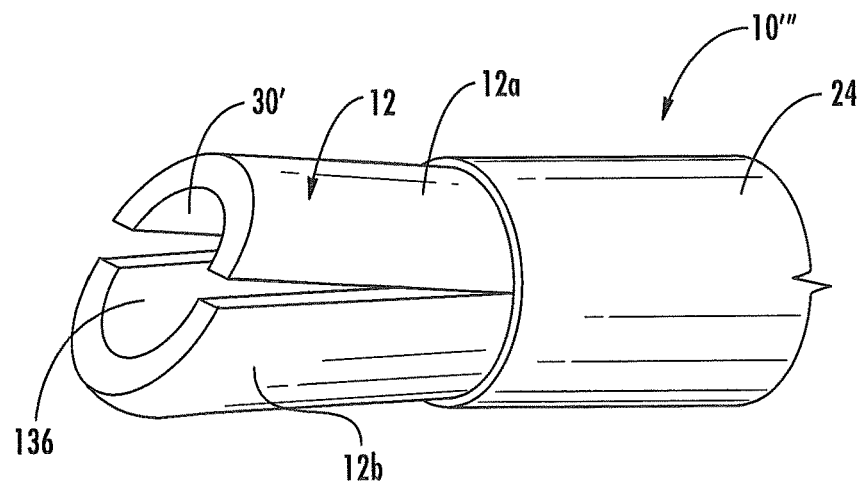
FIG. 34A illustrates a partially open view of the tip shown in FIG. 33.
Figure 34B:
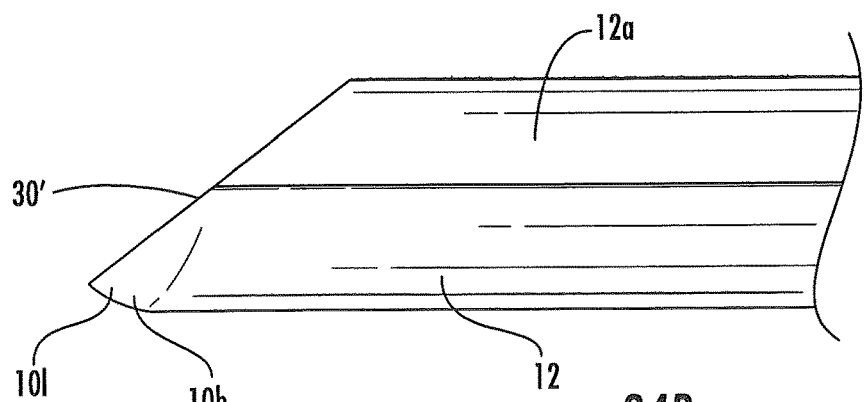
FIG. 34B illustrates the distal end portion of the aspiration member shown in FIG. 34A outside the housing/sleeve and in a closed configuration according to embodiments of the present invention.
Figure 35:
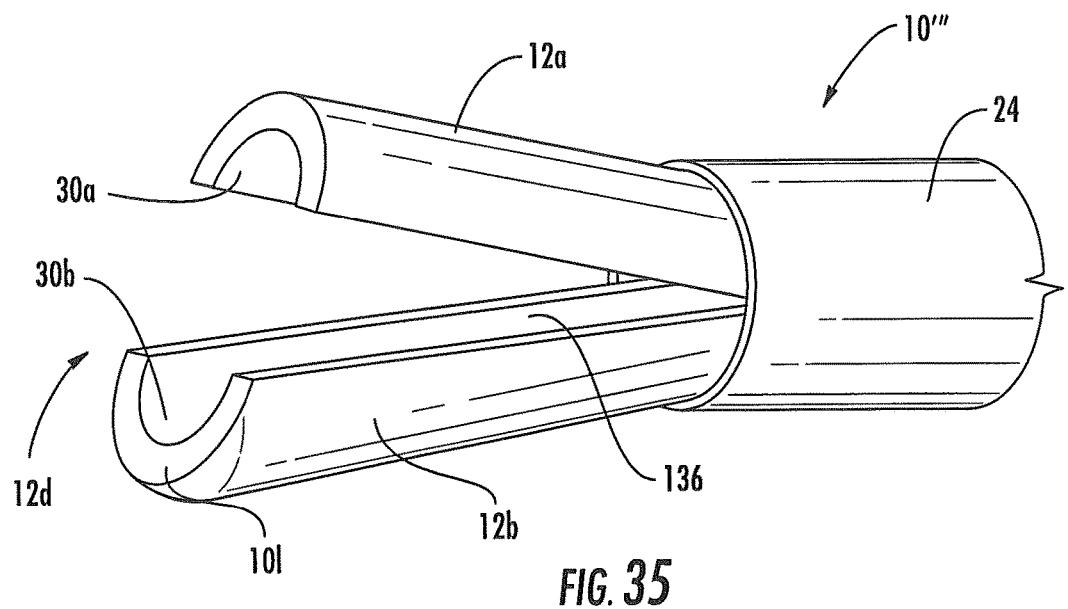
FIG. 35 is a partial end perspective view of the aspiration tip shown in FIGS. 33 and 34A, illustrating a larger open configuration relative to FIG. 34A according to embodiments of the present invention.
Figure 36:
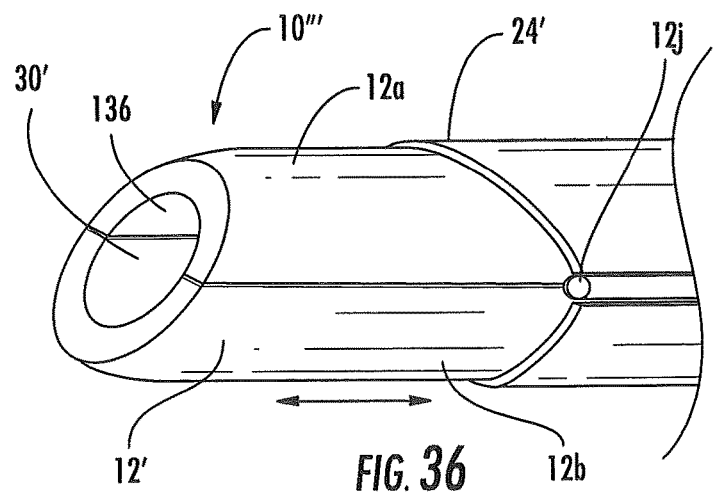
FIG. 36 is a partial distal end view of another aspiration tip similar to that shown in FIG. 34B but with a joint for allowing articulation according to embodiments of the present invention.

FIGS. 33-35 illustrate that the tip 10''' can be configured with first and second cooperating members 12a, 12b that can close together and attach to form a first size aspiration port 230, typically encasing the aspiration channel 136 on a leading end 10l of the tool and can separate to open to form a second larger size aspiration port. In some embodiments, the tip 10''' can cooperate with an outer sleeve 24' to facilitate the open and closing actions. However, other configurations do not require a sleeve. For example, FIG. 36 illustrates a hinged jaw configuration 12j and the sleeve is optional (but may be used with such a configuration). It is contemplated that other tip configurations may be used to allow the open and closing actions.

As shown, the tip 10''' has an inner aspiration member 12' with the sleeve 24' that can slide relative to each other (one or both may slide) so that the inner aspiration member 12' can open and close when the housing, e.g., sleeve 24' resides upstream of the distal end 12d of the aspiration member 12'. The aspiration member 12' has a tip that has an aspiration port or aperture 30'. The aspiration member 12' can be formed as first and second longitudinally extending, cooperating members 12a, 12b that have a distal end 12d that can open and close together.

The members 12a, 12b can be shaped to angle down at the leading end 12d to have a longer (typically flat or curved upward) bottom 10b. The angle can be between about 30-45 degrees, in some embodiments. The (aspiration port) aperture 30' on the distal end 12d can be defined by an open perimeter segment 30a, 30b partially held in each member 12a, 12b and may be circular or have any other geometric shape and is typically between about 0.5 mm to about 0.9 mm in width and/or height, when closed together. In the closed position (FIG. 33), the tip 10''' can aspirate cortex and/or cataract fragments. For larger or tougher fragments, the tip 10''' can be opened to separate the two aspiration members 12a, 12b by sliding the distal tip 12d forward of the sleeve 24 and/or sliding the sleeve 24 rearward away from the distal tip 12d. The tip 10''' can be sized and configured for both phaco-ing large pieces and then gentle enough for smaller cortex pieces.

The cooperating aspiration members 12a, 12b may be configured with a hinge and/or joint 35j (FIG. 36) at a desired position. The hinge/joint 35j can be configured to control the amount of separation or opening and/or the sleeve 24 can have a defined stop position to limit this motion. The amount of longitudinal movement of the sleeve 24 and/or the distal tip 12d is typically between about 1 mm to about 10 mm, more typically between about 1 mm to about 8 mm, such as about 1 mm, about 2 mm, about 3 mm, about 4 mm, about 5 mm, about 6 mm, about 7 mm and about 8 mm. Although not shown, the distal tip 12d can include an external textured polishing surface as discussed and shown above with respect to other embodiments.

The tip 10, 10' and 10'', 10''' can be integrated into the tool and may be metallic or polymeric or combinations of same for assembly to the proximal end or primary body of the tool 20. The tip 10, 10', 10'', 10''' can be integral to the tool 20 or attached or integral to a portion of the tool body 20 rather than provided as a discrete tip component itself.

FIGS. 20A-20G, 21A-21I, 22, 23-29 and 30A-30C illustrate exemplary assemblies with components for some embodiments of the tip 10''. As shown in FIGS. 21A, 20E and 22, for example, the tip 10'' can comprise a primary body 400 that forms the leading edge 10l with the bottom 10b and three sides of the perimeter of the large port 230.

As shown in FIGS. 21A and 22, the body 400 can also define two sides of a door frame 235f with edges forming the guides, channels or rails 401.

Where the tip includes irrigation, the primary body 400 can include irrigation channels 130.

The tip 10'' can be configured with a door 235 and an extension 435 that can be trapped under an upper outer cover 410 with a window 411 having a frame 412 that surrounds and holds the door 235 and sandwiches the side edges of the door 235s and engages the guides, rails or channels 401 (FIG. 22). The primary body 400 can provide the aspiration channel or lumen 136 and attach to the door and extension 235, 435 and cover 410.

The assemblies can also include outer sidewalls 420 that attach to the primary body 400 and may cover the irrigation channels and cooperate with the channels 130 to form the at least one irrigation port 132. The sidewalls 420 can include curved forward ends that form a part of the shape of the exit hole for the irrigation port (FIG. 22).

FIG. 20E illustrates that the primary body 400 can also include a bottom cover 440 the forms a bottom irrigation channel for the forward irrigation port 132f (FIG. 20D, for example).

Figure 30A:
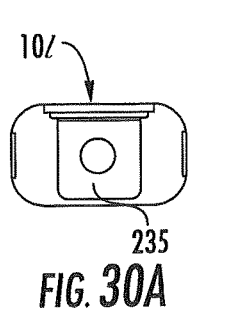
FIGS. 30A-30C are end, side and top scale views of the device shown in FIG. 23.
Figure 30B:
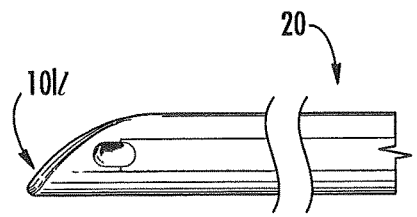
Figure 30C:
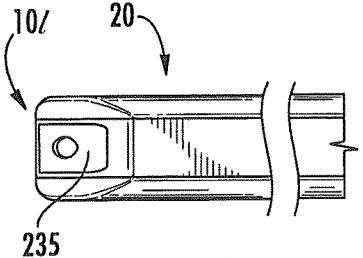

FIGS. 23-29 and 30A-30C illustrate exemplary section and enlarged detail views of an embodiment with the tip 10'' having the door 235 on the open forward leading end. FIGS. 30A-30C are scaled figures according to some embodiments of the invention.

Some or the entire surface of the tip 10'' can be textured 10t for capsular polishing as discussed for other embodiments above. In some embodiments, the texture 10t extends around all or a perimeter of the door frame 235f (FIG. 19A). In some embodiments, the texture 10t resides only on the leading edge at the bottom or floor 10b under the door 235 (as shown by way of example in FIG. 18C with the texture marks). In some embodiments, the texture 10t extends externally both on the bottom and about the perimeter of the door 235. In some embodiments, the texture 10t can also or alternatively be on the external surface of the door 235 (FIG. 21F). In some embodiments, the texture 10t extends on the outer sidewalls 420, and the front of the leading end 10l of the tip 10'' (FIG. 19B). In some embodiments, the tip 10'' is devoid of texture (FIG. 22).

In some embodiments, the tip 10'' is configured so that the opening and closing of the door 235 is for nuclear lens fragments, then the cortex can be removed with the door closed through the smaller port 233 via the aspiration channel 136. Then, the textured surface 10t can be used for capsular polishing, where used or included on the tip of the tool.

Examples of currently available femtosecond laser optical systems are believed to include Alcon LenSx (Alcon Laboratories, Ft Worth, Tex., USA), OptiMedica Catalys (Optimedica Corp, CA, USA), LensAR (LensAR Inc, FL, USA) and Technolas (Technolas Perfect Vision GmbH, Germany). The laser systems typically include an anterior segment imaging system, patient interface and femtosecond laser to image, calculate and deliver the laser pulses. In some embodiments, the surgical tool 10 with the multifunctional tip can be used after or during femtosecond laser surgery to remove nuclear fragments and epinucleus. The textured tip 10t can provide irrigation and/or aspiration port(s) 30 sized and configured to accommodate the larger fragments typically generated by this procedure. The tip 10 can be in communication with an aspiration source (e.g., vacuum) and optionally an ultrasound source 300.

Figure 31:
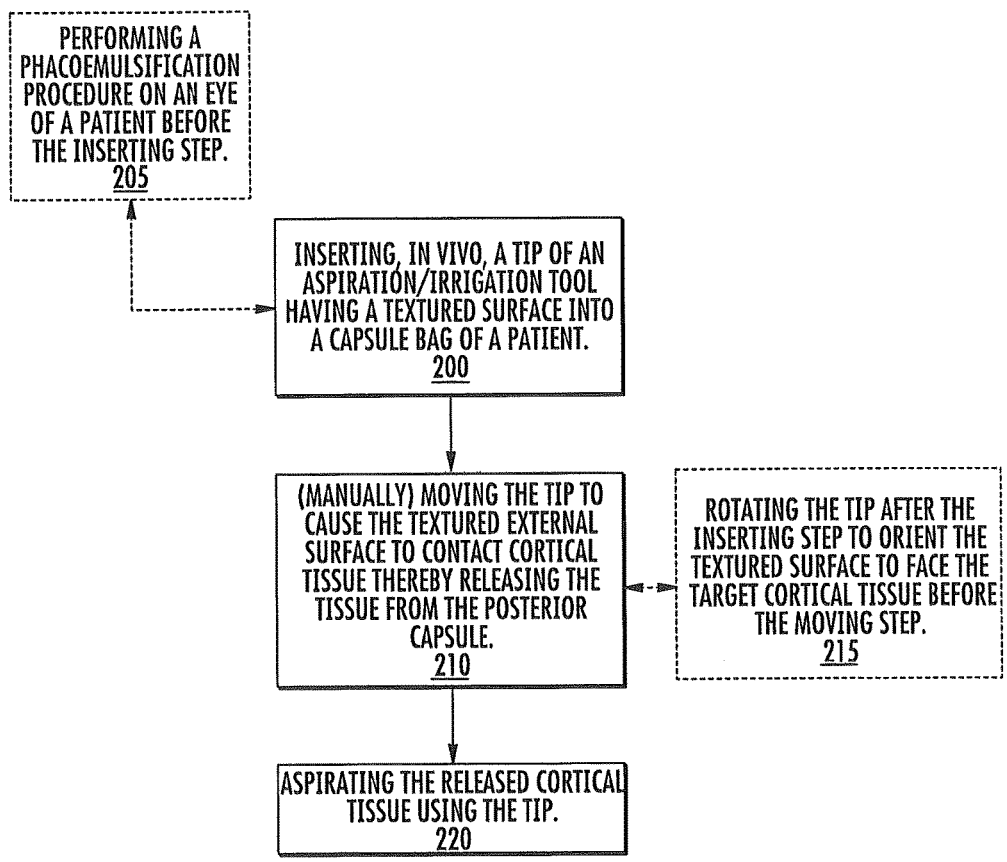
FIG. 31 is a flow chart of exemplary operations that can be used to carry out embodiments of the present invention.

FIG. 31 illustrates operations that can be used to carry out embodiments of the present invention. As shown, a tip of an aspiration/irrigation tool having a textured surface can be inserted, in vivo, into a posterior capsule bag of a patient (block 200). The tip can be (typically manually) moved to cause the textured surface to contact cortical tissue thereby releasing the tissue from the posterior capsule (block 210). The released cortical tissue can be aspirated using the tip (block 220).

The inserting can be carried out after a phacoemulsification procedure and/or laser disintegration procedure is performed on an eye of a patient (block 205).

In some embodiments, the tip can optionally be rotated after the inserting step to orient the textured surface to face the target cortical tissue before the moving step (block 215).

Figure 32:
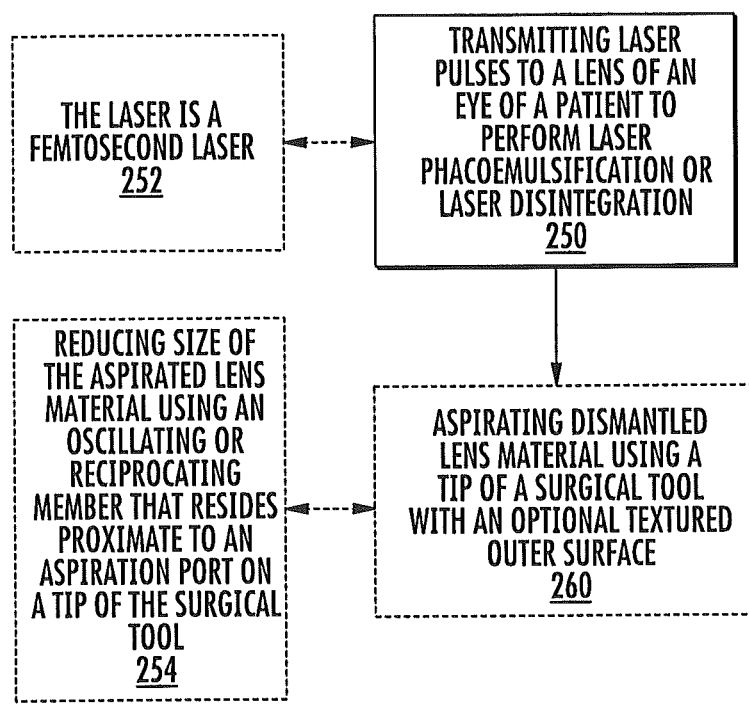
FIG. 32 is a flow chart of exemplary operations that can be used to carry out embodiments of the present invention.

FIG. 32 illustrates exemplary operations of an alternate embodiment of the present invention. In this cataract surgery, a femtosecond laser procedure can be used. The method can include transmitting laser pulses to a lens of an eye of a patient to perform laser phacoemulsification or laser disintegration (block 250). For example, a series of defined laser pulses can be transmitted to a lens of a patient's eye to dismantle the lens. The laser can be a femtosecond laser (block 252) for laser emulsification ("laser phaco") which may eliminate the requirement for ultrasound phaco. The laser may use a modified LASIK laser that is configured to allow for bladeless cataract surgery, such as lasers employing a disk that allows for LASIK systems to be used for cataract surgeries such as the Newsom Bladeless Laser Disk™. In any event, the method includes aspirating dismantled lens material using a tip of a surgical tool with an optional textured outer surface (block 260). The method can include using an oscillating and/or reciprocating member to reduce size of larger lens material prior to suctioning out of an aspiration port (block 254).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, if used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. An aspiration tool for use in combination with a surgical system for cataracts after a phacoemulsification and/or laser disintegration procedure, comprising:

a tip having an open leading end that defines an aspiration port, the open leading end located at a distal most end of the tip, the tip sized and configured for removing cortical and/or nuclear lens fragments, tissue and/or fibers; and a translatable door in communication with the aspiration port configured to extend and retract about the aspiration port, wherein, in an extended position, the door travels forward to occlude the aspiration port, wherein the door has a door aspiration port extending therethrough, the door aspiration port having a size that is smaller than the aspiration port defined by the open leading end, wherein the door is flat across the aspiration port defined by the open leading end to completely close the aspiration port defined by the open leading end, and wherein the door aspiration port resides over the aspiration port defined by the open leading end when the door is in the extended position.

2. The aspiration tool of claim 1, wherein the open leading end, when viewed from the side, has a tapered or acute angled profile.

3. The aspiration tool of claim 1, wherein the open leading end of the tip has an external planar bottom surface.

4. The aspiration tool of claim 1, wherein the aspiration port defined by the open leading end has a wall with a perimeter that has spaced apart sides with guides, channels or rails that engage outer side edges of the door to allow the door to slidably translate up and down.

5. The aspiration tool of claim 1, wherein the door has a planar bottom end that is sized and configured to close against a surface of the open leading end of the tip.

6. The aspiration tool of claim 1, wherein at least a portion of the open leading end of the tip comprises a textured exterior surface.

7. The aspiration tool of claim 6, wherein the textured exterior surface extends about at least a portion of a perimeter of the door and/or an external wall of the open leading end of the tip adjacent the perimeter of the door.

8. The aspiration tool of claim 1, the tool further comprising a user control in communication with the door, wherein the door is configured to oscillate or reciprocate over the aspiration port defined by the open leading end, and wherein the user control comprises at least one of an electronic or manual control.

9. The aspiration tool of claim 1, wherein the door is flexible and extends to be flat across the aspiration port defined by the open leading end when partially and/or fully closed.

10. The aspiration tool of claim 1, wherein the door has a pair of laterally opposing outer side edges that each slidably engage a respective side door frame in the tip during longitudinal reciprocal movement.

11. The aspiration tool of claim 1, wherein the open leading end of the tip comprises a front irrigation port that resides adjacent and to a side or under or over the aspiration port defined by the open leading end to thereby allow irrigation fluid to flow forward out of the front irrigation port during aspiration.

12. The aspiration tool of claim 1, wherein the tip comprises an elongate primary body defining an interior aspiration channel, the body comprising a pair of spaced apart longitudinally extending guides, channels or rails that extend downward towards the distal most end of the tip to define first and second sides of a door frame for slidably engaging respective outer spaced apart sides of the door.

13. The aspiration tool of claim 12, wherein the door has a longitudinally extending shaft or extension that cooperates with the longitudinally extending guides, channels or rails and a user control to translate the door between the extended position and a retracted position.

14. An aspiration tool for use in combination with a surgical system for cataracts after a phacoemulsification and/or laser disintegration procedure, comprising:
   a tip having an open leading end that defines an aspiration port, the tip sized and configured for removing cortical and/or nuclear lens fragments, tissue and/or fibers; and
   a translatable door in communication with the aspiration port configured to extend and retract about the aspiration port, wherein, in an extended position, the door travels forward to at least partially occlude the aspiration port,
   wherein the door has a door aspiration port extending therethrough, the door aspiration port having a size that is smaller than the aspiration port defined by the open leading end,
   wherein the aspiration port defined by the open leading end has a width that is between about 1 mm to about 1.5 mm across and a height that is between about 0.7 mm to about 1 mm.

15. The aspiration tool of claim 14, wherein the door is flat across the aspiration port defined by the open leading end to close the aspiration port defined by the open leading end, and wherein the door aspiration port resides over the aspiration port defined by the open leading end when the door is in the extended position.

\* \* \* \* \*

UNITED STATES PATENT AND TRADEMARK OFFICE
CERTIFICATE OF CORRECTION

PATENT NO. : 10,213,533 B2
APPLICATION NO. : 14/483626
DATED : February 26, 2019
INVENTOR(S) : Keith Andrew Walter Page 1 of 1

It is certified that error appears in the above-identified patent and that said Letters Patent is hereby corrected as shown below:

In the Claims

Column 20, Claim 8, Line 44:
Please correct "the open leading end and" to read -- the open leading end in response to input with the user control and --

Signed and Sealed this
Second Day of July, 2019

Andrei Iancu
*Director of the United States Patent and Trademark Office*